US007386089B2

(12) United States Patent
Endo et al.

(10) Patent No.: US 7,386,089 B2
(45) Date of Patent: Jun. 10, 2008

(54) RADIOGRAPHIC IMAGING APPARATUS, CONTROL METHOD THEREOF, AND RADIOGRAPHIC IMAGING SYSTEM

(75) Inventors: Tadao Endo, Honjyo (JP); Toshio Kameshima, Kumagaya (JP); Tomoyuki Yagi, Honjyo (JP); Katsuro Takenaka, Kodama-gun (JP); Keigo Yokoyama, Honjyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/450,577

(22) Filed: Jun. 12, 2006

(65) Prior Publication Data

US 2006/0289774 A1    Dec. 28, 2006

(30) Foreign Application Priority Data

Jun. 14, 2005   (JP)   ............................. 2005-174095
Jun. 6, 2006    (JP)   ............................. 2006-157467

(51) Int. Cl.
    *G01N 23/00*      (2006.01)
(52) U.S. Cl. ........................ 378/5; 378/98.11; 378/114
(58) Field of Classification Search ............. 378/4–20, 378/91, 98.8, 98.9, 98.11, 98.12, 101, 111, 378/112, 114, 115
    See application file for complete search history.

(56) References Cited

U.S. PATENT DOCUMENTS

| | | | |
|---|---|---|---|
| 4,361,901 A | 11/1982 | Daniels et al. | |
| 4,432,370 A | 2/1984 | Hughes et al. | |
| 4,837,686 A | 6/1989 | Sones et al. | |
| 6,393,097 B1 * | 5/2002 | Aufrichtig et al. | ....... 378/98.11 |
| 6,396,898 B1 * | 5/2002 | Saito et al. | .................... 378/19 |
| 6,904,119 B2 * | 6/2005 | Oikawa | ...................... 378/15 |
| 6,952,015 B2 | 10/2005 | Kameshima | ............ 250/370.11 |
| 6,952,464 B2 | 10/2005 | Endo | ........................ 378/98.11 |
| 6,985,555 B2 | 1/2006 | Endo | ........................ 378/98.11 |

(Continued)

FOREIGN PATENT DOCUMENTS

EP        1 387 320 A2     2/2004

(Continued)

OTHER PUBLICATIONS

European Search Report dated Mar. 30, 2007, issued in European application No. 06115172.61-1265.

*Primary Examiner*—Jurie Yun
(74) *Attorney, Agent, or Firm*—Fitzpatrick, Cella, Harper & Scinto

(57) ABSTRACT

A radiographic imaging apparatus includes a radiation detection circuit with elements arranged two-dimensionally to convert radiation into an electrical signal, a driving mechanism which changes a positional relationship between the components, a memory which stores that electrical signal, an imaging controller to control the radiation source so as to emit a first radiation pulse at a first energy for a first frame and to emit a second radiation pulse at a second energy for a second frame, controlling the driving mechanism to maintain the positional relationship during the first radiation pulse and the second radiation pulse and to change the positional relationship in a period between the first period and the second period. The frames are different and sequentially imaged, and an image processing unit for subtraction processing of the first and second frames in memory to generate a processed image, then generate a tomographic and a 3D image.

16 Claims, 17 Drawing Sheets

U.S. PATENT DOCUMENTS

| | | | |
|---|---|---|---|
| 7,002,157 B2 | 2/2006 | Kameshima | 250/370.11 |
| 7,012,260 B2 | 3/2006 | Endo | 250/370.11 |
| 7,138,639 B2 | 11/2006 | Kameshima | 250/370.11 |
| 7,154,099 B2 | 12/2006 | Endo | 250/370.11 |
| 7,227,926 B2 | 6/2007 | Kameshima et al. | 378/98.9 |
| 7,272,429 B2 * | 9/2007 | Walker et al. | 600/407 |
| 2004/0101090 A1 | 5/2004 | Drummond et al. | |
| 2005/0109927 A1 | 5/2005 | Takenaka et al. | 250/252.1 |
| 2005/0199834 A1 | 9/2005 | Takenaka et al. | 250/580 |
| 2005/0200720 A1 | 9/2005 | Kameshima et al. | 348/220.1 |
| 2005/0220269 A1 | 10/2005 | Endo et al. | 378/114 |
| 2005/0264665 A1 | 12/2005 | Endo et al. | 348/308 |
| 2006/0119719 A1 | 6/2006 | Kameshima | 348/308 |
| 2006/0192130 A1 | 8/2006 | Yagi | 250/370.14 |
| 2007/0040099 A1 | 2/2007 | Yokoyama et al. | 250/208.1 |
| 2007/0069144 A1 | 3/2007 | Kameshima | 250/370.09 |
| 2007/0080299 A1 | 4/2007 | Endo et al. | 250/370.09 |
| 2007/0096032 A1 | 5/2007 | Yagi et al. | 250/370.11 |
| 2007/0125952 A1 | 6/2007 | Endo et al. | 250/369 |
| 2007/0131843 A1 | 6/2007 | Yokoyama et al. | 250/205 |

FOREIGN PATENT DOCUMENTS

| | | |
|---|---|---|
| EP | 1 426 903 A2 | 6/2004 |
| JP | 04-343836 | 11/1992 |
| JP | 05-224322 | 9/1993 |
| JP | 08-116044 | 5/1996 |

* cited by examiner

REFRESH MODE

PHOTOELECTRIC CONVERSION MODE

SATURATED STATE

RADIOGRAPHIC IMAGING APPARATUS, CONTROL METHOD THEREOF, AND RADIOGRAPHIC IMAGING SYSTEM

FIELD OF THE INVENTION

The present invention relates to a radiographic imaging apparatus, a control method thereof, and a radiographic imaging system.

BACKGROUND OF THE INVENTION

Conventional X-ray imaging systems installed in hospitals are classified into film radiography and digital radiography. In film radiography, a patient is irradiated with X-rays, and the X-rays that have passed through the patient are exposed to a film. In digital radiography, X-rays that have passed through a patient are converted into an electrical signal, and the electrical signal is detected as a digital value by using an A/D converter and stored in a memory.

An example of the current mainstream of the latter digital radiography is disclosed in Japanese Patent Laid-Open No. 5-224322. In this scheme, an X-ray image is formed on a photostimulable phosphor called an imaging plate (IP) using BaBr:Eu as a typical material. Then, the IP is scanned with a laser beam, and visible light from the IP is converted into an electrical signal, i.e., digitized by using, e.g., a photomultiplier.

According to a scheme disclosed in Japanese Patent Laid-Open No. 8-116044, a phosphor is irradiated with X-rays. Visible light emitted in proportion to the X-ray dose is converted into an electrical signal, i.e., digitized by a photosensor made of amorphous silicon. The typical materials of the phosphor are $Gd_2O_2S:Tb$ and CsI:Tl. This device is called an FPD (Flat Panel Detector). Some FPDs use, as the material, Se or $PbI_2$ that directly absorbs X-rays and converts them into an electrical signal instead of using the phosphor.

There is also a device which irradiates a primary phosphor with X-rays. Photoelectrons from the phosphor surface are accelerated and focused by an electron lens, and a phosphor image (X-ray image) on a secondary phosphor surface is converted into an electrical signal by a camera tube or CCD. This is a general scheme called an image intensifier (I.I.) and used for fluorography. It is a digital radiographic scheme capable of detecting an electrical signal as a digital value.

As described above, there exist a variety of devices for digitizing an X-ray image, and a demand for them is increasingly growing in recent years. When image data can be digitized, radiographic data can easily be recorded, displayed, printed, and stored. Hence, the need for digitization in the medical field is increasing.

In the recent medical field which is shifting from film radiography, i.e., so-called analog radiography to the above-described digital radiography, plain X-ray imaging is performed as the first step of X-ray imaging. For, e.g., a chest part, the imaging is called chest plain X-ray imaging, and X-ray imaging of the front (or side) of the chest part of a human body is done. To cover the whole chest part (upper part) of a human body, a radiography area of 14"×17" size (35 cm×43 cm) or more and, more preferably, an area of 43 cm×43 cm or more is necessary. In the chest plain X-ray imaging, the FPD is a more promising digital radiography scheme than I.I. which has a problem of distortion of a peripheral image.

When plain radiography is executed as the first step of X-ray imaging, the doctor diagnostically reads the radiographed image. If a shadow is recognized, CT is generally executed as the second step of X-ray imaging. CT is performed to obtain a tomographic image of the part recognized by plain radiography. The radiation dose of CT is generally larger than that of plain radiography. For this reason, CT is executed only after plain radiography or equivalent tests except a few cases such as emergency.

In the CT, normally, X-rays from an X-ray tube are focused by a collimator, and a patient is irradiated with X-rays called a fan beam having a fan shape. Transmission light is detected by using X-ray detection elements which are arranged on the opposite side of the patient to detect the X-rays. The CT is executed while making the set of the X-ray tube and X-ray detection elements helically rotate around the radiographic part of the patient. Obtained image data is reconstructed to 3D image data by using a computer.

In the CT using the fan beam, X-ray detection elements arranged in a liner array direction or in several lines are used, and much time is required from the start to the end of radiography. For this reason, the burden on the patient who is fixed to restrict motion and let stand in a closed space called a gantry for a long time becomes heavy. There are also a problem of high power consumption and a problem of the life of the X-ray tube (a problem of replacement frequency). To solve these problems, Japanese Patent Laid-Open No. 4-343836 uses a large-area X-ray detection element including X-ray detection elements arranged two-dimensionally. This prior art also proposes a method of obtaining a CT image by executing helical scan while irradiating a patient with cone-beam X-rays.

In the chest plain X-ray imaging, internal information near the lung field of the upper body, including the gullet, trachea, pulmonary vessels, alveoli, heart, cardiac vessels, diaphragm, ribs, and collar bones, can be radiographed in one image by X-ray imaging of one cycle. Hence, the chest plain X-ray imaging is frequently used as a useful radiographic method to screen a lesion (morbid portion).

In the conventional chest plain X-ray imaging, a fluoroscopic image is observed because of its principle. Hence, if the morbid portion to be observed is located, e.g., behind a rib, cardiac vessel, or diaphragm, the fluoroscopic images overlap, and the shadow of the morbid portion is hard to find out. This decreases the morbid portion screening efficiency and delays finding of the morbid portion.

The same problems as described above also arise in the conventional X-ray CT. For example, when a to-be-detected morbid portion having a very low contrast is present near an internal structure such as a bone with a very high contrast, even a specialist in diagnostic reading can hardly perceive the morbid portion. Additionally, the conventional CT apparatus executes radiography while making a patient pass through a large special rotation mechanism called a gantry incorporating X-ray detection elements and an X-ray source. Since the arrangement itself is different from general radiographic apparatuses, there is a possibility that the CT apparatus is located in another room. This decreases the radiography efficiency.

SUMMARY OF THE INVENTION

The present invention has been made in consideration of the above described problems, and has as its object to provide a radiographic imaging apparatus, a control method thereof, and a radiographic imaging system which detect a morbid portion with a low contrast and increase the diagnostic efficiency.

According to the present invention, there is provided a radiographic imaging apparatus comprising a radiation detection circuit in which a plurality of conversion elements to convert radiation emitted from a radiation source and transmitted through an object into an electrical signal are arranged two dimensionally, a driving mechanism which changes a positional relationship between the object and the radiation source and the radiation detection circuit, a memory which stores, as image data, the electrical signal detected by the radiation detection circuit, an imaging controller configured to control the radiation source so as to emit a first radiation pulse at a first energy when imaging a first frame and to emit a second radiation pulse at a second energy when imaging a second frame, and to control said driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period, wherein the second frame is different from the first frame and the first and second frames are sequentially imaged, and an image processing unit which executes subtraction processing of image data of the first frame and image data of the second frame stored in said memory to generate a processed image and generates one of a tomographic image and a 3D image of the object by using the processed image.

According to another aspect of the present invention, there is provided a radiographic imaging apparatus comprising a radiation detection circuit in which a plurality of conversion elements to convert radiation emitted from a radiation source and transmitted through an object into an electrical signal are arranged two dimensionally, a driving mechanism which changes a positional relationship between the object and the radiation source and the radiation detection circuit, a memory which stores, as image data, the electrical signal detected by the radiation detection circuit, an imaging controller configured to control the radiation source so as to emit a first radiation pulse at a first energy when imaging a first frame and to emit a second radiation pulse at a second energy when imaging a second frame, and to control the driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period, wherein the second frame is different from the first frame and the first and second frame are sequentially imaged, and an image processing unit configured to generate at least two of a first image based on image data of the first frame stored in the memory, a second image based on image data of the second frame stored in the memory, and a processed third image based on image data obtained by executing energy subtraction processing for the image data of the first frame and the image data of the second frame and display the generated image on a display device.

According to the present invention, there is provided a radiographic imaging system comprising the above-described radiographic imaging apparatus, signal processing means for processing a signal from the radiographic imaging apparatus, display means for displaying the signal from the signal processing means, and transmission means for transmitting the signal from the signal processing means.

According to the present invention, there is provided a control method of a radiographic imaging apparatus including a radiation detection circuit in which a plurality of conversion elements to convert radiation emitted from a radiation source and transmitted through an object into an electrical signal are arranged two dimensionally, a driving mechanism which changes a positional relationship between the object and the radiation source and the radiation detection circuit, and a memory which stores, as image data, the electrical signal detected by the radiation detection circuit, comprising steps of controlling the radiation source so as to emit a first radiation pulse at a first energy when imaging a first frame and to emit a second radiation pulse at a second energy when imaging a second frame, wherein the second frame is different from the first frame and the first and second frame are sequentially imaged; and controlling the driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period; and executing subtraction processing of image data of the first frame and image data of the second frame stored in said memory to generate a processed image and generating one of a tomographic image and a 3D image of the object by using the processed image.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

The preferred embodiments of the present invention will be described below with reference to the accompanying drawings. In the preferred embodiments of the present invention, X-rays are used as radiation. However, the radiation is not limited to X-rays and also includes electromagnetic waves such as α-rays, β-rays, and γ-rays.

First Embodiment

Figure 1:
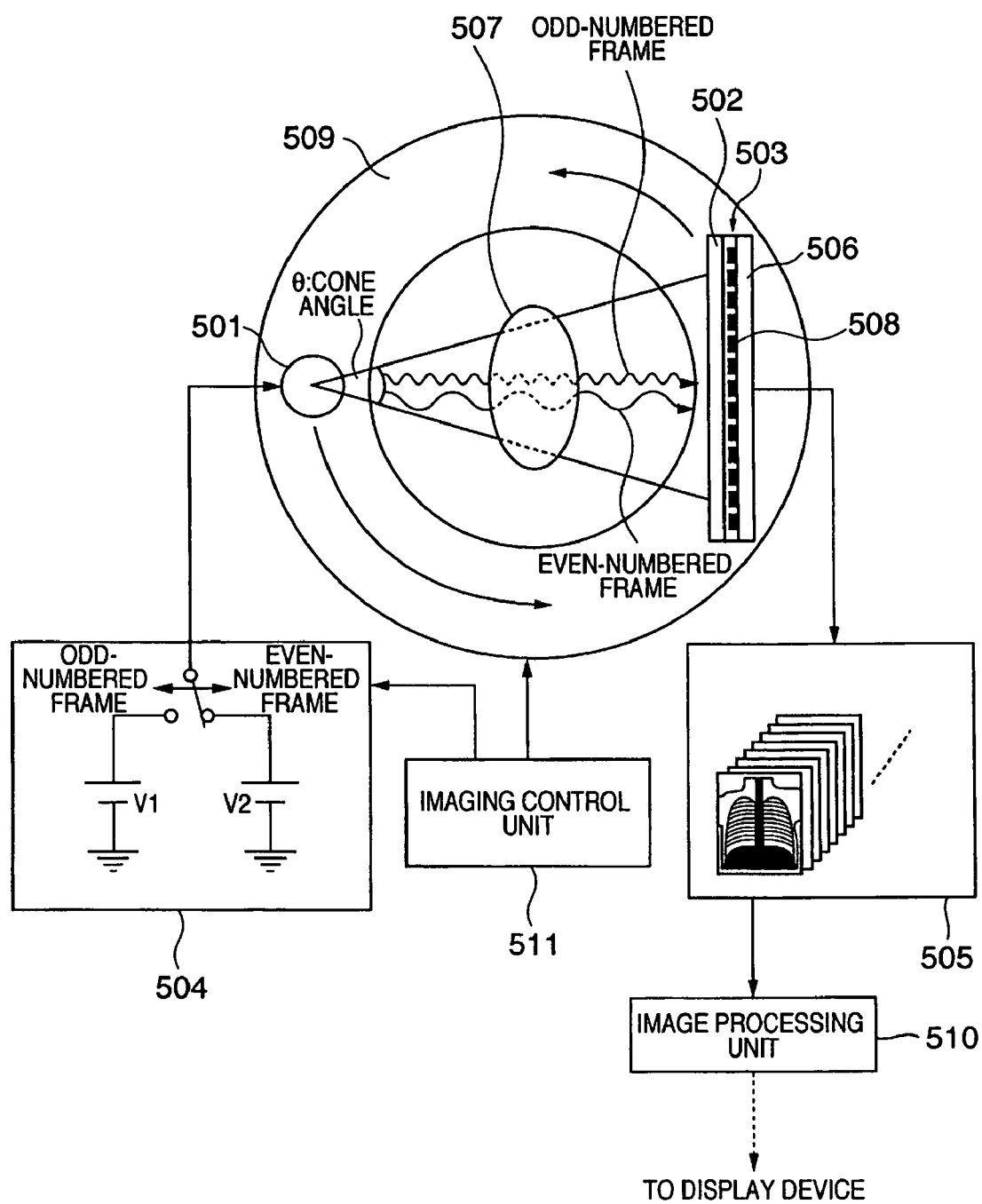
FIG. 1 is a view showing the schematic arrangement of an X-ray imaging apparatus according to the preferred first embodiment of the present invention.

FIG. 1 is a view showing the schematic arrangement of an X-ray imaging apparatus according to the preferred first embodiment of the present invention.

An object 507 is irradiated with X-rays which are emitted from an X-ray tube 501 and have an exit angle θ. The object 507 is mainly a human (patient). The X-rays transmitted through the object 507 are converted into visible light by a phosphor 502. The visible light from the phosphor 502 is converted into an electrical signal by conversion elements 508. As a result, an X-ray image of the object 507 is obtained as an electrical signal.

An example of the material of the conversion elements 508 is amorphous silicon. The conversion elements 508 are formed on an insulating substrate 506 such as a glass substrate. The phosphor 502 to convert X-rays into visible light and the conversion elements 508 substantially adhere to each other by, e.g., bonding or the like so that an X-ray detection circuit 503 including the phosphor 502 and conversion elements 508 is formed. The phosphor 502 is made of a material containing at least one of, e.g., $Gd_2O_2S$, $Gd_2O_3$, CsI as the main component. An X-ray power supply 504 supplies a voltage to the X-ray tube 501. The X-ray power supply 504 supplies a high voltage to accelerate electrons in the X-ray tube 501.

This embodiment is designed to convert incident X-rays into visible light by the phosphor 502. Without using the phosphor 502, incident X-rays may be absorbed by the conversion elements 508, and the absorbed X-rays may directly be converted into an electrical signal. In this case, the conversion elements 508 are made of a material containing at least one of, e.g., lead iodide, mercury iodide, selenium, cadmium telluride, gallium arsenide, gallium phosphide, zinc sulfide, and silicon as the main component.

A memory 505 stores, as digital data, the electrical signal (image signal) of the object 507 converted by the X-ray detection circuit 503 and has an area to store image data of a plurality of frames. The image data stored in the memory 505 is subjected to arithmetic processing such as energy subtraction processing and reconstruction processing to obtain a tomographic image by an image processing unit 510 so that an image for display or diagnosis is generated. More specifically, the image processing unit 510 executes the above-described processing for the image data of an odd-numbered (2m−1)th (m is a natural number; m≧1) frame and the image data of an even-numbered (2m)th frame to generate a tomographic image or 3D image of the object 507.

In the X-ray imaging apparatus of this embodiment, in executing temporally continuous radiography for a plurality of frames (n frames), an imaging control unit 511 switches the voltage to be supplied from the X-ray power supply 504 to the X-ray tube 501 between odd-numbered frame radiography and even-numbered frame radiography. The wavelength of X-rays is changed to change the energy of the X-rays emitted from the X-ray tube 501 so that the X-ray detection circuit 503 detects an image signal of the object 507 whose X-ray absorption of the internal structure changes. The detected image signal is converted into a digital signal by an A/D converter (not shown) and stored in the memory 505 as image data. In the example shown in FIG. 1, a voltage V1 is supplied from the X-ray power supply 504 to the X-ray tube 501 in odd-numbered frame radiography, while a voltage V2 is supplied in even-numbered frame radiography under the control of the imaging control unit 511. Hence, X-rays with a short wavelength are emitted from the X-ray tube 501 to the object 507 in odd-numbered frame radiography, while X-rays with a long wavelength are emitted in even-numbered frame radiography.

As shown in FIG. 1, the X-ray detection circuit 503 and X-ray tube 501 can rotate around the object 507 in a pair (integrally). A gantry 509 serves as a rotation mechanism and has a doughnut-shaped hole to pass the object 507 at the center. That is, the gantry 509 functions as a driving mechanism to change the positional relationship between the object 507 and the X-ray tube 501 and X-ray detection circuit 503. Continuous radiography is repeatedly executed as the pair of X-ray tube 501 and X-ray detection circuit 503 finely rotate in the gantry 509 under the control of the imaging control unit 511. X-rays from the X-ray tube 501 are emitted in a point shape. The X-rays are not particularly focused by, e.g., a collimator. Hence, a conical beam having the exit angle (cone angle) θ is formed which is normally called a "cone beam". A fluoroscopic image of the object 507 irradiated with the cone beam is detected by the X-ray detection circuit 503.

The rotation angle of the X-ray tube 501 and X-ray detection circuit 503 with respect to the object 507 in the gantry 509 is 180° or 360°. When the image processing unit 510 processes transmitted X-ray image data obtained by 180° rotation, a tomographic image of the object 507 is obtained. When the image processing unit 510 processes transmitted X-ray image data obtained by 360° rotation, reconstruction takes more time because the information amount in the object 507 is larger than the tomographic image obtained by 180° rotation. However, a tomographic image with a higher quality is obtained in general. On the other hand, in obtaining a tomographic image of, e.g., a chest part, the patient (object 507) must hold the breath. In 360° rotation, the burden on the patient is heavy because the breath holding time is long.

In the X-ray imaging apparatus of this embodiment, radiography is executed while changing the wavelength of X-rays emitted from the X-ray tube 501 between odd-numbered frame radiography and even-numbered frame radiography. That is, image data in the memory 505 includes different fluoroscopic images for odd- and even-numbered frames. For example, the image processing unit 510 executes energy subtraction processing by using the first and second images, thereby creating one original image data serving as the base of a tomographic image. The image processing unit 510 also executes energy subtraction processing by using the third and fourth images, thereby creating one original image data serving as the base of a tomographic image. Similarly, energy subtraction processing is executed up to the nth image. If n is an even number, (n/2) original image data are created as the base of tomographic images. If n is an odd number, {(n−1)/2} original image data are created without using the last image.

Generally, in plain radiography of an object, a method has been implemented in which radiography is performed while changing the voltage to be supplied to the X-ray tube 501, and subtraction processing is executed for two X-ray image data, thereby deleting the shadow of, e.g., a bone part. This processing is called energy subtraction processing (ES processing), as described above. This radiography method utilizes the fact that when the wavelength of incident X-rays changes, the X-ray absorbance changes between bone tissue and soft tissue such as blood vessels, lymphatic vessels, and nerves. In this embodiment, the above-described energy subtraction processing is not limited to simple subtraction. The energy subtraction processing will be described below.

Let D1(V1) be the image density of a rib component and D2(V1) be the image density of a blood vessel component, which are obtained by radiographing an odd-numbered frame by the tube voltage V1. Let D1(V2) be the image density of the rib component and D2(V2) be the image density of the blood vessel component, which are obtained by radiographing an even-numbered frame by the tube voltage V2.

If the image density ratio of the rib component is D1(V2)/D1(V1)=1, the rib shadow can be removed by simple subtraction processing (F(2m)−F(2m−1)). However, when the energy of X-rays changes, the X-ray absorption of the bone component (or even any other part) changes so that an image density difference is generated. That is, the image density ratio of the rib component is not D1(V2)/D1(V1)=1. Assume that the image density ratio of the rib component is D1(V2)/D1(V1)=k1. In this case, the rib shadow can be removed by subtraction processing F(2m)−[k1×F(2m−1)].

On the other hand, the tissue (component) of a blood vessel is different from that of a rib. For this reason, the image density ratio of the blood vessel component is D2(V2)/D2(V1)=k2≠k1. Even when subtraction processing F(2m)−[k1×F(2m−1))] is executed, the blood vessel image is extracted without disappearing. In this subtraction processing, F(2m−1) is operated (multiplied by k1) and subtracted from F(2m). If, e.g., k1=1.5, an image obtained by multiplying F(2m−1) by 3 may be subtracted from an image obtained by multiplying F(2m) by 2. That is, the result does not change even when an image obtained by operating F(2m−1) is subtracted from an image obtained by operating F(2m). In the above-described example, a rib shadow is removed. Conversely, subtraction processing of removing a blood vessel shadow may be executed. The subtraction operation is selected in accordance with the tissue lesion to be observed.

In radiography of this embodiment, the transmission thickness of X-rays incident from the front of the object 507 is different from that of X-rays incident from a side of the object. Hence, the formula of energy subtraction processing is preferably changed in some instances. That is, the energy subtraction processing need not always be constant and may be changed depending on the angle. Preferably, several processing methods are prepared in accordance with the image quality requirement and selected on the basis of the purpose.

In subtraction data (original image data) corresponding to ½ of taken pictures, for example, a bone shadow is removed. When the original image data is reconstructed, a tomographic image containing no bone shadow with a high contrast can be obtained. When the bone shadow is removed, a morbid portion with a very low contrast in the vicinity can be detected at a high probability. As a tomographic image display method, for example, a normal tomographic image obtained by reconstructing the image data of odd-numbered frames (or a normal tomographic image obtained by reconstructing the image data of even-numbered frames) and a tomographic image obtained by reconstructing original image data that has undergone energy subtraction processing are displayed simultaneously on a single screen for comparison. In this case, the diagnostic reading work efficiency and diagnostic efficiency increase. Instead of removing a bone shadow, a tomographic image of a bone may be created by removing soft tissue by energy subtraction processing.

Generally, radiolucent data (voxel) in a small region in the object 507 is obtained from a number of image data obtained by X-ray tomography. Hence, not only a tomographic image but also a 3D image can be displayed. In this embodiment, to say nothing of a normal 3D image, a 3D image which has undergone energy subtraction processing to remove, e.g., a bone shadow can also be displayed by processing of the image processing unit 510. The two 3D images can be displayed side by side for comparison.

Figure 2:
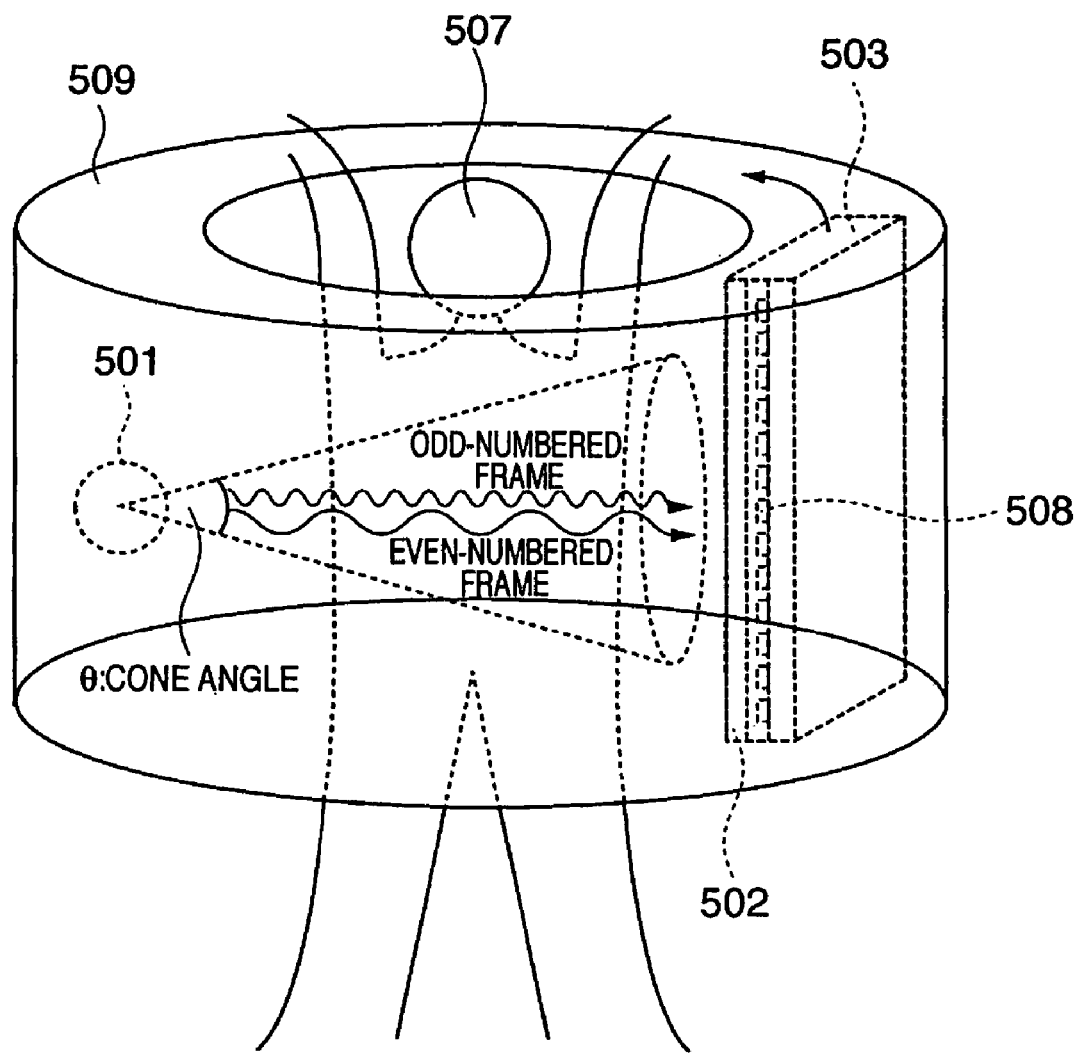
FIG. 2 is a perspective view showing the schematic arrangement of the X-ray imaging apparatus according to the preferred first embodiment of the present invention.

FIG. 2 is a perspective view showing the schematic arrangement of the X-ray imaging apparatus according to the preferred first embodiment of the present invention. The object 507 is generally a human (patient). Radiography is executed while keeping the object 507 arranged inside the gantry 509. The object 507 normally lies on a table, although not illustrated.

The conversion elements 508 are two-dimensionally arranged in the X-ray detection circuit 503. The X-ray detection circuit 503 with a size of about 40 cm square has already been developed for chest plain radiography. If amorphous silicon is used as the material of the conversion elements 508, the X-ray detection circuit 503 having an area of, e.g., 60 to 80 cm square or more can be formed. Along with recent demand for liquid crystal TVs, CVD apparatuses and photolithography apparatuses for manufacturing amorphous silicon larger than 180 cm square are available. An X-ray imaging apparatus that is as large as the object 507 can be formed by using the manufacturing technologies. However, when the area of the X-ray detection circuit increases, the reading speed (frame rate) generally tends to be low.

Figure 3:
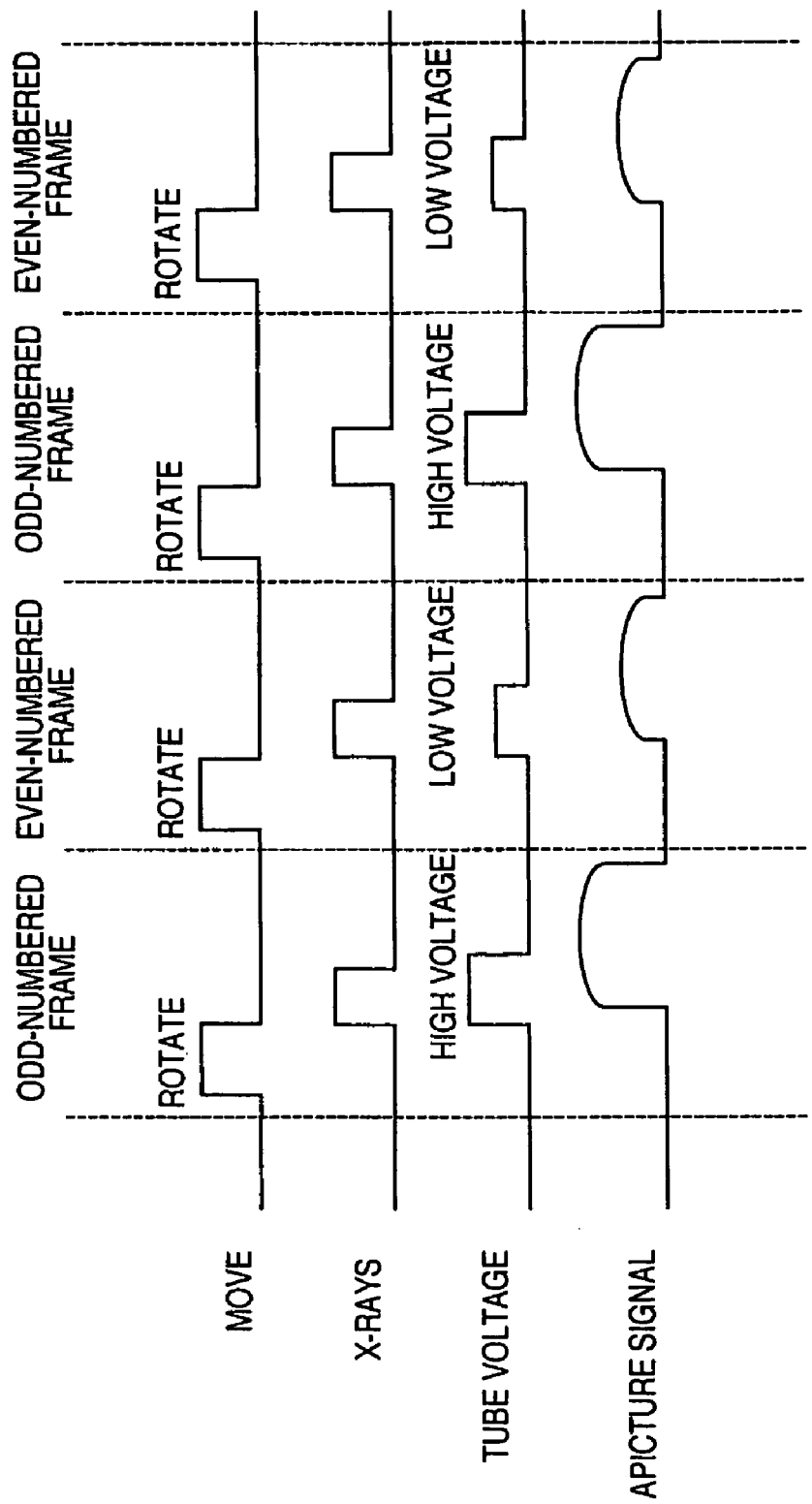
FIG. 3 is a timing chart showing the operation of the X-ray imaging apparatus according to the preferred first embodiment of the present invention.

FIG. 3 is a timing chart showing the operation of the X-ray imaging apparatus according to the preferred first embodiment of the present invention.

The timing chart in FIG. 3 shows four signals: "move", "X-rays", "tube voltage" and "picture signal" in radiographing odd- and even-numbered frames. "Move" indicates the timing of movement (displacement) of the pair of X-ray tube 501 and X-ray detection circuit 503, which rotates around the object 507. In this case, the reading operation is repeated while moving the X-ray tube 501 and X-ray detection circuit 503 in radiographing each frame independently of whether the frame is odd-numbered or even-numbered. "Tube voltage" is set to be high in odd-numbered frame radiography and low in even-numbered frame radiography. "Picture signal" is output after "X-rays" are emitted in a pulse shape.

As shown in FIG. 3, in this embodiment, the positional relationship between the object 507 and the X-ray tube 501 and X-ray detection circuit 503 is changed between odd-numbered frame radiography and even-numbered frame radiography. The positional relationship in radiography changes between two consecutive frames. However, no problem is posed by energy subtraction processing if the moving amount is very small.

Figure 4:
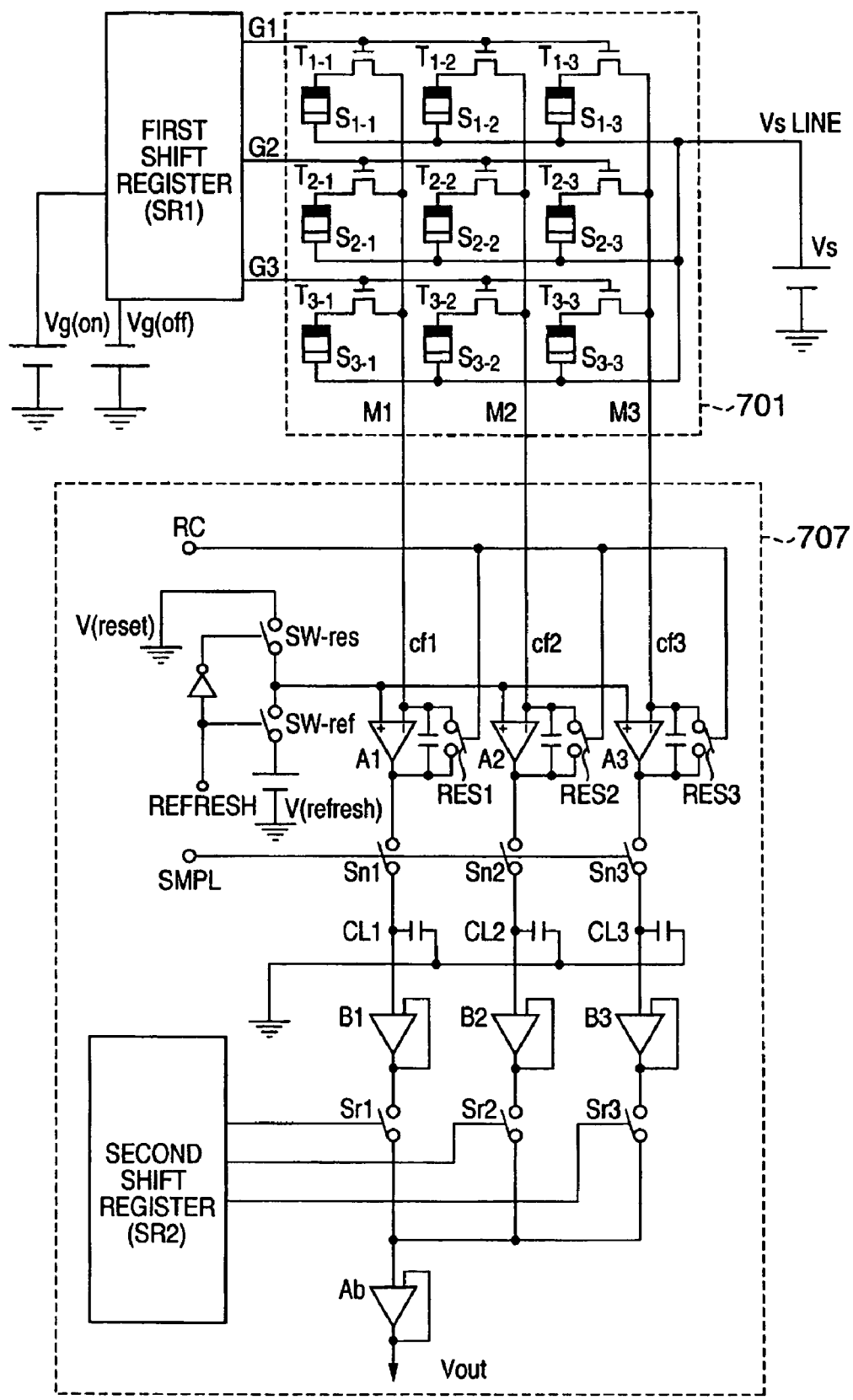
FIG. 4 is a circuit diagram of an X-ray detection circuit of the X-ray imaging apparatus according to the preferred first embodiment of the present invention.

FIG. 4 is a circuit diagram of the X-ray detection circuit 503 of the X-ray imaging apparatus according to the preferred first embodiment of the present invention.

The X-ray detection circuit 503 comprises a conversion circuit 701 and a reading circuit 707. For the descriptive convenience, 3×3=9 pixels are arranged in the conversion circuit 701 shown in FIG. 4. However, the present invention is not limited to this, and an arbitrary number of pixels can be arranged.

In the conversion circuit 701, reference symbols S1-1 to S3-3 denote conversion elements such as MIS photoelectric conversion elements; T1-1 to T3-3, switching elements such as TFTs; G1 to G3, gate wiring lines to turn on/off the switching elements; and M1 to M3, signal wiring lines. A Vs line is a wiring line to apply a storage bias to the conversion elements S1-1 to S3-3. The solidly shaded electrode in each of the conversion elements S1-1 to S3-3 is a G electrode. A D electrode is formed on the opposite side. The D electrodes are shared by parts of the Vs line. To make light incident, a thin N+ layer is used as the D electrode. The Vs line is biased by a power supply Vs. A first shift register SR1 applies a driving pulse voltage to the gate wiring lines G1 to G3. A voltage Vg(on) to turn on the switching elements (T1-1 to T3-3) and a voltage Vg(off) to turn off the switching elements (T1-1 to T3-3) are supplied from the outside to the first shift register SR1.

The reading circuit 707 reads parallel signal outputs from the conversion circuit 701 and converts them into a serial output. The signal wiring lines M1 to M3 are connected to the inverting terminals (−) of operational amplifiers A1 to A3, respectively. Capacitive elements Cf1 to Cf3 are connected between the inverting terminals (−) and the output terminals. When the switching elements (T1-1 to T3-3) are turned on, the capacitive elements Cf1 to Cf3 integrate currents flowing from the conversion elements S1-1 to S3-3 to the capacitive element sides, thereby converting the currents into voltages. Switches RES1 to RES3 reset the capacitive elements Cf1 to Cf3 to a reset bias V(reset). The switches RES1 to RES3 are connected in parallel to the capacitive elements Cf1 to Cf3. In FIG. 4, the reset bias V(reset) is indicated by 0 V, i.e., GND.

Sample-and-hold capacitances CL1 to CL3 temporarily store signals stored in the operational amplifiers A1 to A3 or capacitive elements Cf1 to Cf3. Reference symbols Sn1 to Sn3 denote switches for sample and hold; B1 to B3, buffer amplifiers; and Sr1 to Sr3, switches to convert parallel signals into a serial signal. A second shift register SR2 applies a pulse for serial conversion to the switches Sr1 to Sr3. A buffer amplifier Ab outputs the converted serial signal. A switch SW-res resets the noninverting terminals of the operational amplifiers A1 to A3 to the reset bias V(reset) (0 V in FIG. 4). A switch SW-ref refreshes the noninverting terminals of the operational amplifiers A1 to A3 to a refresh bias V(refresh). These switches are controlled by a signal "REFRESH". More specifically, when the signal "REFRESH" is "Hi", the switch SW-ref is turned on. On the other hand, when the signal "REFRESH" is "Lo", the switch SW-res is turned on. These switches are never turned on simultaneously.

Figure 5:
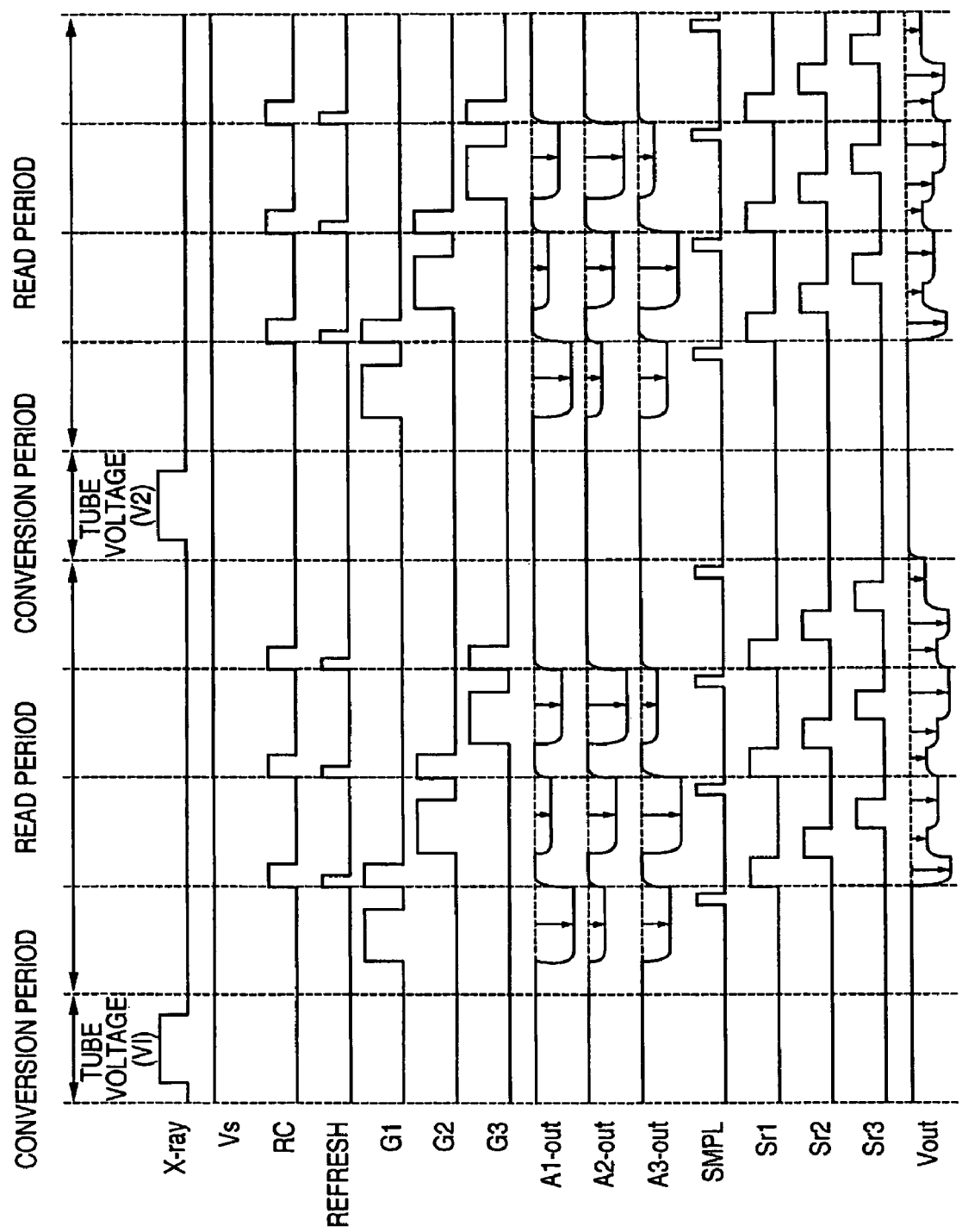
FIG. 5 is a timing chart showing the operation of the X-ray detection circuit shown in FIG. 4.

FIG. 5 is a timing chart showing the operation of the X-ray detection circuit shown in FIG. 4.

FIG. 5 shows the operation of the X-ray detection circuit 503 for two frames. In FIG. 5, X-rays of the first pulse (X-rays in first frame radiography) and X-rays of the second pulse (X-rays in second frame radiography) are expressed likewise for the illustrative convenience. In this embodiment, however, the X-ray energy changes between the first pulse and the second pulse. In moving image radiography, the timing chart shown in FIG. 5 is continuously repeated in accordance with the number of taken pictures. The tube voltage of the X-ray power supply 504 is switched to change the X-ray energy between odd-numbered frame radiography and even-numbered frame radiography.

The conversion period will be described.

In the conversion period, the D electrodes of all the conversion elements S1-1 to S3-3 are biased to the reading power supply Vs (positive potential). All the signals from the first shift register SR1 are "Lo" so that all the switching elements (T1-1 to T3-3) are OFF. In this state, an X-ray pulse is emitted from the X-ray tube 501. The D electrodes (N+ electrodes) of the conversion elements are irradiated with visible light through the phosphor 502. Carriers, i.e., electrons and holes are generated in the i-layer of each conversion element. The generated electrons are moved to the D electrode by the power supply Vs. On the other hand, the holes are stored in the interface between the i-layer and the insulating layer of each of the conversion elements S1-1 to S3-3. The holes are held even after the X-rays from the X-ray tube 501 stop.

The read period will be described.

The operation in the read period is performed in the conversion elements S1-1 to S1-3 of the first row, the conversion elements S2-1 to S2-3 of the second row, and the conversion elements S3-1 to S3-3 of the third row in this order.

To read out charges (image signals) of the conversion elements S1-1 to S1-3 of the first row, the first shift register SR1 applies a gate pulse to the gate wiring line G1 of the switching elements (T1-1 to T1-3) of the first row. The high level of the gate pulse equals the externally supplied voltage Vg(on). The switching elements (T1-1 to T1-3) of the first row are turned on. The charges stored in the conversion elements S1-1 to S1-3 of the first row flow as currents through the switching elements (T1-1 to T1-3) of the first row. The currents are input to the capacitive elements Cf1 to Cf3 connected to the operational amplifiers A1 to A3 and integrated.

Read capacitances are added to the signal wiring lines M1 to M3, although not particularly illustrated in FIG. 4. The charges in the conversion elements S1-1 to S1-3 of the first row are transferred to the read capacitance side through the switching elements (T1-1 to T1-3) of the first row. However, the signal wiring lines M1 to M3 are virtually grounded by the reset bias (GND) of the noninverting terminals (+) of the operational amplifiers A1 to A3. Since no potential change by the transfer operation occurs, the signal wiring lines M1 to M3 are held to GND. That is, the charges in the conversion elements S1-1 to S1-3 of the first row are transferred to the capacitive elements Cf1 to Cf3.

The output thermals of the operational amplifiers A1 to A3 change as shown in FIG. 5 in accordance with the charge amounts in the conversion elements S1-1 to S1-3 of the first row. Since the switching elements (T1-1 to T1-3) of the first row are turned on simultaneously, the outputs from the operational amplifiers A1 to A3 change simultaneously. That is, parallel output occurs. When a signal "SMPL" is turned on in this state, the output signals from the operational amplifiers A1 to A3 are transferred to the sample-and-hold capacitances CL1 to CL3. When the signal SMPL is turned off, the signals are temporarily held.

Next, when the second shift register SR2 applies a pulse to the switches Sr1, Sr2, and Sr3 in this order, the charges held in the sample-and-hold capacitances CL1 to CL3 are output from the amplifier Ab in the order of CL1, CL2, and CL3. As a result, the charges (image signals) of the conversion elements S1-1 to S1-3 of the first row are sequentially converted into a serial signal and output. The charge (image signal) read operation of the conversion elements S2-1 to S2-3 of the second row and the charge (image signal) read operation of the conversion elements S3-1 to S3-3 of the third row are also executed in the same way.

The charges of the conversion elements S1-1 to S1-3 of the first row are output from the conversion circuit 701 when the output signals from the operational amplifiers A1 to A3 are sampled and held by the sample-and-hold capacitances CL1 to CL3 in accordance with the signal SMPL for the conversion elements. Hence, while serial conversion and output are being done by the switches Sr1 to Sr3 in the reading circuit 707, the refresh operation of the conversion elements S1-1 to S1-3 of the first row in the conversion circuit 701 and the reset operation of the capacitive elements Cf1 to Cf3 can be executed.

The refresh operation of the conversion elements S1-1 to S1-3 of the first row is achieved by changing the signal "REFRESH" to "Hi" to turn on the switch SW-ref, electrically connecting the switches RES1 to RES3 by a signal "RC", and applying the voltage vg(on) to the gate wiring line G1 of the switching elements (T1-1 to T1-3) of the first row. That is, the G electrodes of the conversion elements S1-1 to S1-3 of the first row are refreshed to the refresh bias V(refresh) by the refresh operation. Then, the reset operation is executed.

In the reset operation, while keeping the voltage Vg(on) applied to the gate wiring line G1 of the switching elements (T1-1 to T1-3) of the first row and the switches RES1 to RES3 electrically connected, the signal "REFRESH" is changed to "Lo". With this operation, the G electrodes of the conversion elements S1-1 to S1-3 of the first row are reset to the reset bias V(reset)=GND. Simultaneously, the charges stored in the capacitive elements Cf1 to Cf3 are reset. After the reset operation is ended, a gate pulse can be applied to the gate wiring line G2. That is, simultaneously as the serial conversion operation by the second shift register SR2 is being executed for the charges of the conversion elements S1-1 to S1-3 of the first row, the conversion elements S1-1 to S1-3 of the first row are refreshed, and the capacitive elements Cf1 to Cf3 are reset. Then, the charges of the conversion elements S2-1 to S2-3 of the second row can be transferred to the signal wiring lines M1 to M3 by the first shift register SR1.

With the above-described operation, the charges (image signals) of all the conversion elements S1-1 to S3-3 of the first to third rows can be output. When the operation for one frame is repeated a plurality of number of times, continuous images can be acquired.

Figure 6:
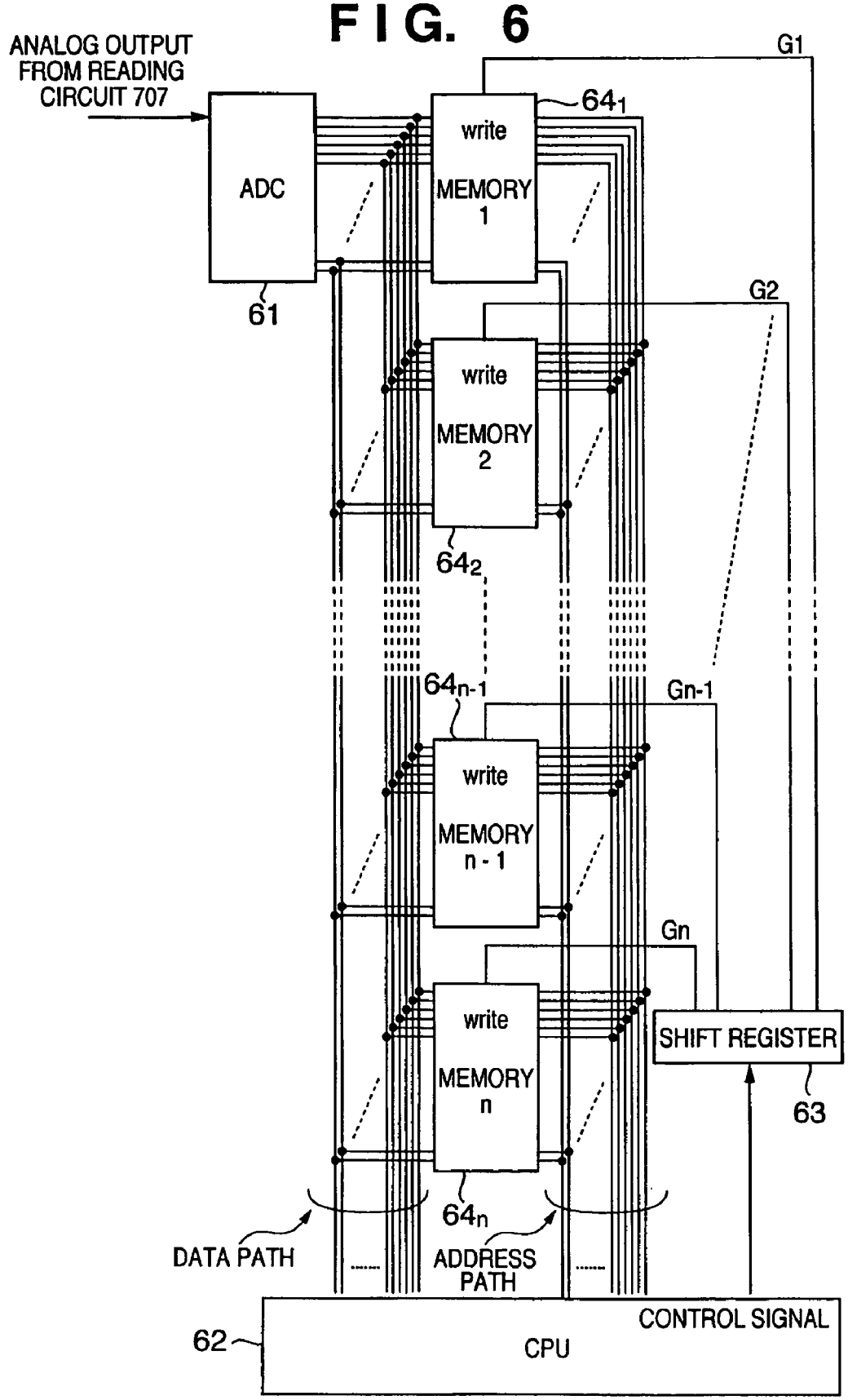
FIG. 6 is a block diagram of components which process an analog signal output from a reading circuit shown in FIG. 4 in the X-ray imaging apparatus according to the preferred first embodiment of the present invention.

FIG. 6 is a block diagram of components which process an analog signal output from the reading circuit shown in FIG. 4 in the X-ray imaging apparatus according to the preferred first embodiment of the present invention.

FIG. 6 shows, as components, an A/D converter (ADC) 61, CPU 62, shift register 63, and memory units $64_1$ to $64_n$. In this embodiment, for example, the A/D converter (ADC) 61 is included in the X-ray detection circuit 503. The memory units $64_1$ to $64_n$ are included in the memory 505. The CPU 62 and shift register 63 are included in the image processing unit 510.

The A/D converter (ADC) 61 converts an analog signal output from the reading circuit 707 into a digital signal. The memory units $64_1$ to $64_n$ store, as image data, image signals of the first frame (F1) to the nth frame (Fn).

The analog signal output from the reading circuit 707 is input to the A/D converter (ADC) 61. The resolution of the A/D converter (ADC) 61 changes depending on the diagnostic purpose. In chest X-ray imaging, the resolution is appropriately 12 to 14 bits or more. The digital signal from the A/D converter (ADC) 61 is stored in the memory units $64_1$ to $64_n$ as image data for each frame. In FIG. 6, n memory units are arranged which store image data corresponding to radiography of the first frame (F1) to the nth frame (Fn). Signals from the memory units are processed by the CPU (Central Processing Unit) 62. The processing includes energy subtraction processing and reconstruction processing to obtain a tomographic image.

Figure 7:
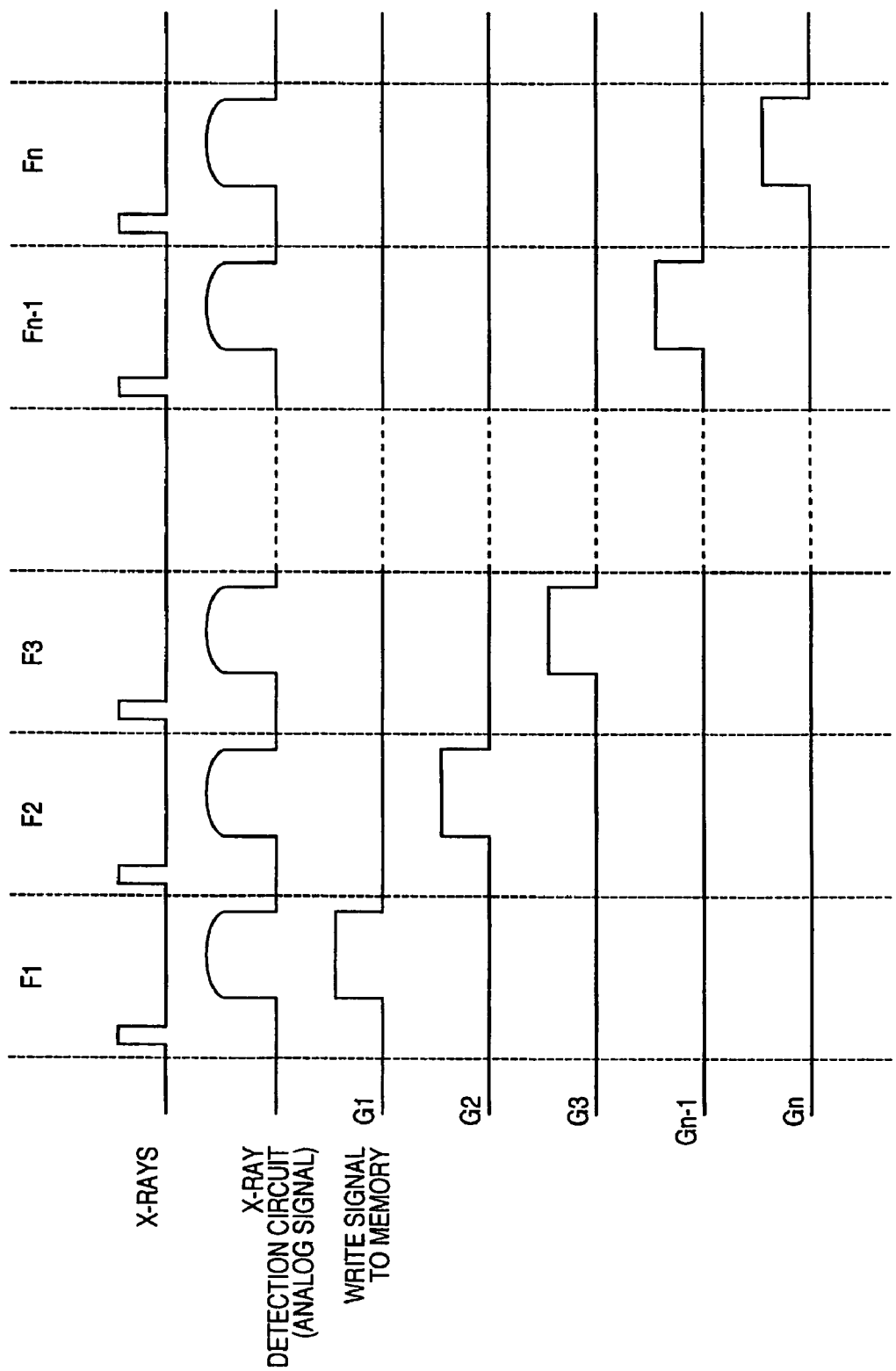
FIG. 7 is a timing chart showing the operation of a CPU shown in FIG. 6.

FIG. 7 is a timing chart showing the operation of the CPU 62 shown in FIG. 6. The timing chart also includes the X-ray generation timing of each of the frames (F1, . . . , Fn−1, Fn).

Figure 8:
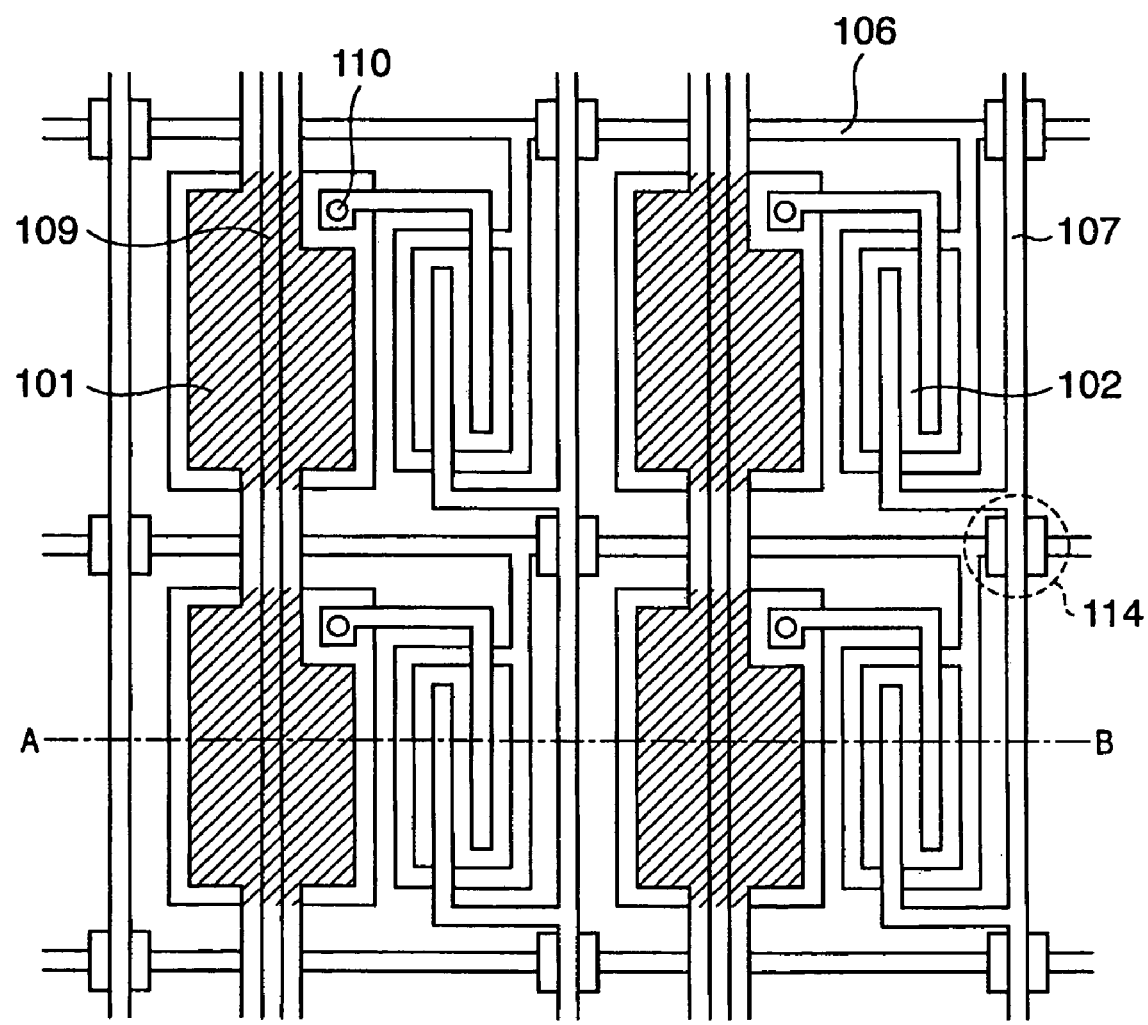
FIG. 8 is a plan view showing the schematic arrangement of a conversion circuit shown in FIG. 4.

FIG. 8 is a plan view showing the schematic arrangement of the conversion circuit 701 shown in FIG. 4.

Figure 9:
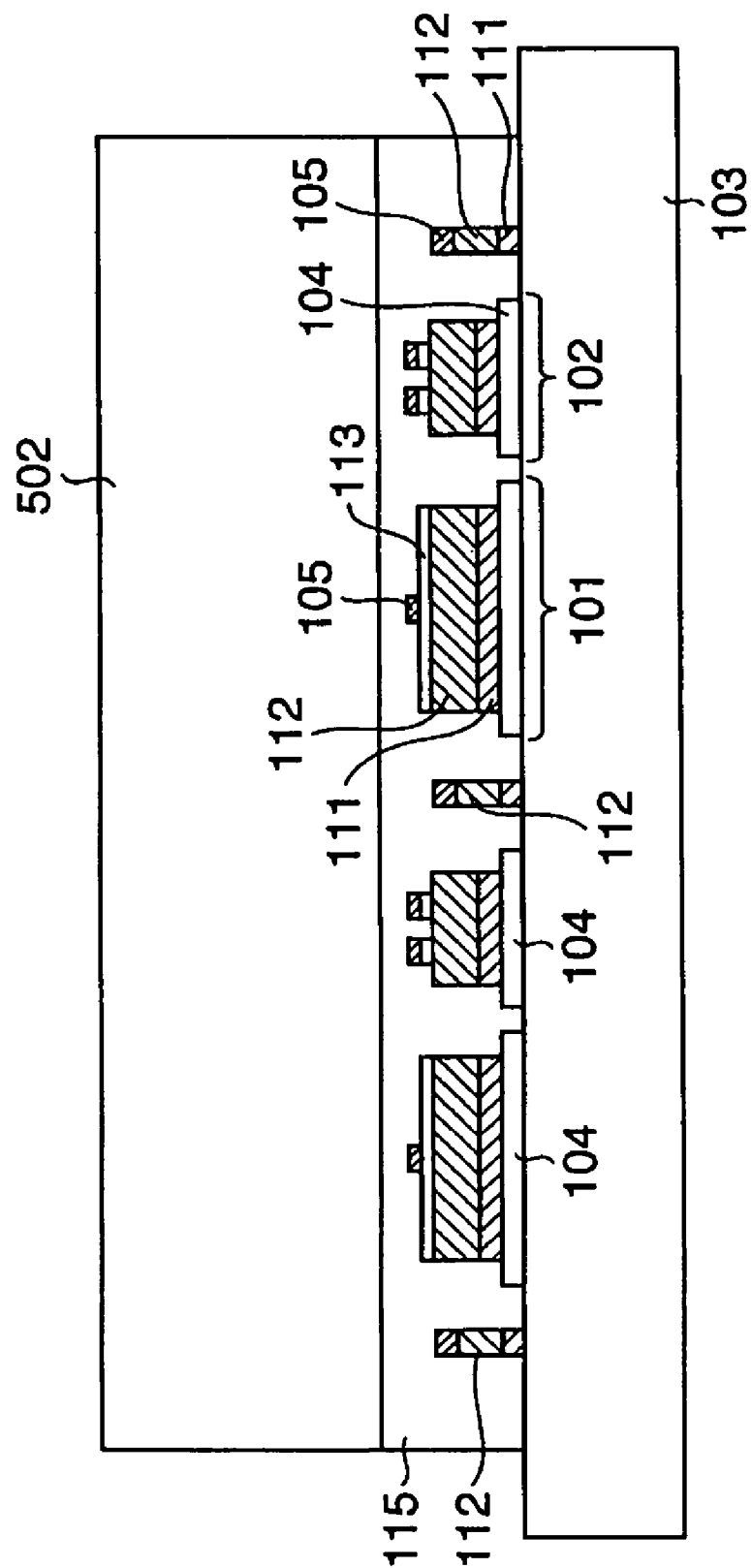
FIG. 9 is a sectional view of the conversion circuit taken along a line A-B in FIG. 8.

Conversion elements 101 correspond to the conversion elements S1-1 to S3-3 in FIG. 4. Switching elements 102 correspond to the switching elements (T1-1 to T3-3) in FIG. 4. The conversion elements 101 and switching elements 102 are formed using an amorphous silicon thin film. FIG. 8 also shows interconnections to connect them. FIG. 9 is a sectional view of the conversion circuit 701 taken along a line A-B in FIG. 8. To simplify the description, a MIS photoelectric conversion element will simply be referred to as a conversion element hereinafter.

The conversion elements 101 and switching elements 102 (amorphous silicon switching elements which will simply be referred to as switching elements hereinafter) are formed on a single insulating substrate 103. The lower electrodes of the conversion elements 101 are formed from a first metal thin-film layer 104 which is also shared by the lower electrodes (gate electrodes) of the switching elements 102. The upper electrodes of the conversion elements 101 are formed from a second metal thin-film layer 105 which is also shared by the upper electrodes (source and drain electrodes) of the switching elements 102.

The first metal thin-film layer 104 and second metal thin-film layer 105 are also shared by gate driving wiring lines 106 and matrix signal wiring lines 107 in the conversion circuit 701 shown in FIG. 8. Referring to FIG. 8, 2×2=4 pixels are arranged in total. However, the present invention is not limited to this, and an arbitrary number of pixels can be arranged. The hatched regions in FIG. 8 correspond to the light-receiving surfaces of the conversion elements 101. A power supply line 109 applies a bias to the conversion elements. A contact hole portion 110 connects a conversion element to a switching element. The matrix signal wiring lines 107 are arranged above the gate driving wiring lines 106 so as to cross them at wiring cross portions 114.

As shown in FIGS. 8 and 9, when a structure mainly made of amorphous silicon is used, the conversion elements 101, switching elements 102, gate driving wiring lines 106, and matrix signal wiring lines 107 can be formed on the single insulating substrate 103 by the single process. Hence, the conversion circuit 701 with a large area can easily be provided at a low cost.

The device operation of one conversion element 101 will be described next.

Figure 10A:
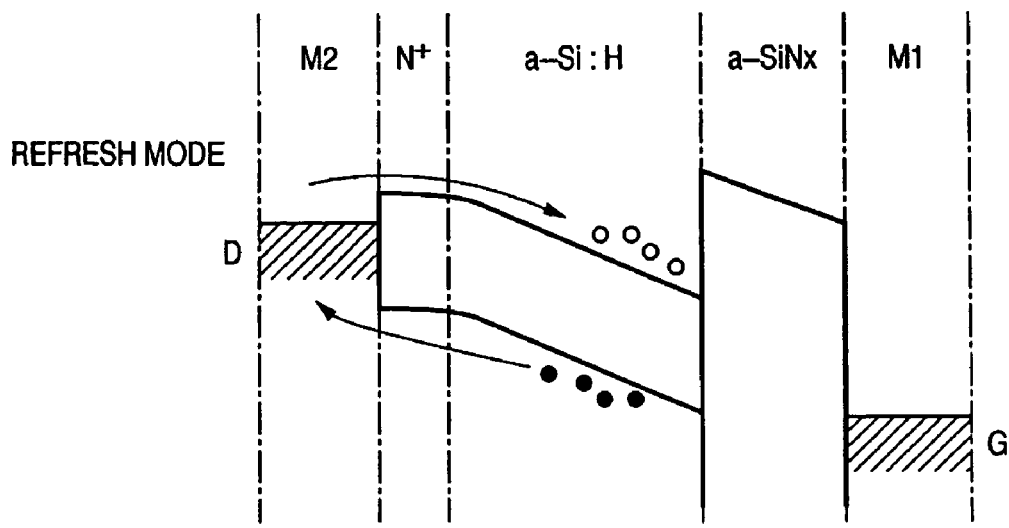
FIGS. 10A to 10C are energy band charts for explaining the device operation of a conversion element.
Figure 10B:
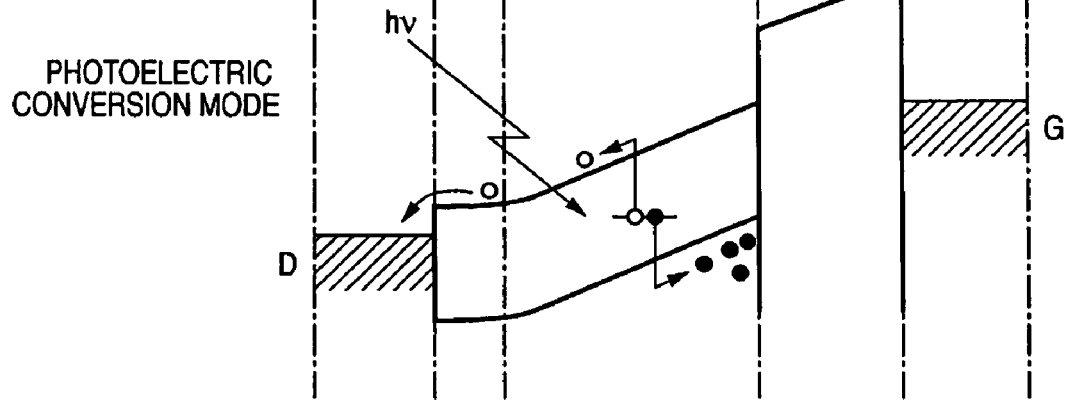
Figure 10C:
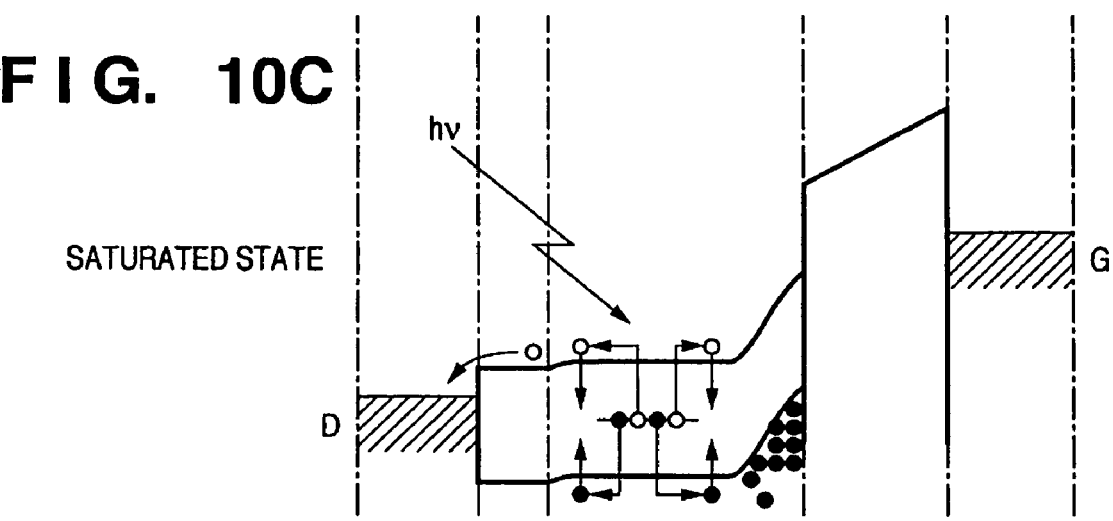

FIGS. 10A to 10C are energy band charts for explaining the device operation of the conversion element 101.

FIGS. 10A and 10B show the operation in the refresh mode and the operation in the conversion mode, respectively. FIG. 10C shows the operation in a saturated state. M1 and M2 shown on the sides of FIGS. 10A to 10C indicate the thickness-direction states of the layers in FIG. 9.

More specifically, M1 indicates the lower electrode (G electrode) formed from the first metal thin-film layer 104 (e.g., Cr) in FIG. 9. An amorphous silicon nitride (a-SiN$_x$) layer corresponds to an a-SiN insulating thin-film layer 111 in FIG. 9 which inhibits passage of electrons and holes. The a-SiN$_x$ layer must be so thick as to prevent the tunnel effect and is normally set to 500 Å or more. An amorphous silicon hydride (a-Si:H) layer corresponds to an a-Si semiconductor thin-film layer 112 in FIG. 9. This is a conversion semiconductor layer formed from an intrinsic semiconductor layer (i-layer). An N+ layer corresponds to an N+ layer 113 in FIG. 9. This is a single-conductivity-type carrier injection inhibition layer which is formed from an amorphous semiconductor such as N-type a-Si:H to inhibit hole injection to the a-Si:H layer. M2 indicates the upper electrode (D electrode) formed from the second metal thin-film layer 105 (e.g., Al) in FIG. 9.

In FIG. 9, the second metal thin-film layer 105 (D electrode) does not completely cover the N+ layer 113. However, electrons freely move between the D electrode and the N+ layer 113. Hence, the D electrode and N+ layer 113 are always at equipotential. The following description will be done assuming this condition.

The conversion element 101 has two operation modes, i.e., the refresh mode and conversion mode corresponding to the manner a voltage is applied to the D electrode or G electrode.

In FIG. 10A showing the refresh mode, a negative voltage relative to the G electrode is applied to the D electrode. Holes indicated by filled circles in the i-layer are guided to the D electrode by the electric field. Simultaneously, electrons indicated by open circles are injected to the i-layer. At this time, several holes and electrons recombine and vanish in the N+ layer and i-layer. If this state continues for a sufficiently long time, the holes in the i-layer are removed from there.

To change the refresh mode to the conversion mode shown in FIG. 10B, a positive potential relative to the G electrode is applied to the D electrode. Electrons in the i-layer are guided to the D electrode instantaneously. However, since the N+ layer acts as an injection inhibition layer, holes are not guided to the i-layer. When light becomes incident on the i-layer in this state, the light is absorbed, and electron-hole pairs are generated. The generated electrons are guided to the D electrode by the electric field. The holes move in the i-layer and reach the interface between the i-layer and the a-SiN$_x$ layer. The holes cannot move into the a-SiN$_x$ layer and therefore stay in the i-layer. At this time, since the electrons move to the D electrode, and the holes move to the interface between the i-layer and a-SiN$_x$ layer, a current flows from the G electrode to maintain the electroneutrality in the conversion element 101. The current corresponds to the electron-hole pairs generated by the light. Hence, the current is proportional to the incident light.

After the conversion mode shown in FIG. 10B is maintained for a certain period, the refresh mode is set again. The holes staying in the i-layer are guided to the D electrode, as described above. Simultaneously, a current corresponding to the holes flows. The amount of holes corresponds to the total amount of light incident during the conversion mode. At this time, a current corresponding to the amount of electrons injected to the i-layer also flows. This amount is almost constant and can be detected by subtraction. That is, the conversion element 101 can output the amount of light that becomes incident in real time and simultaneously detect the total amount of light that has become incident for a certain period.

However, if the conversion mode prolongs or the illuminance of incident light is high due to some reason, no current flows despite light incidence. This is because a saturated state is generated, as shown in FIG. 10C. In the saturated state, many holes stay in the i-layer, and the electric field in the i-layer becomes small due to the holes. For this reason, generated electrons are not guided, and instead, recombine with the holes in the i-layer. If the light incident state changes in the saturated state, a current may flow unstably. When the mode changes to the refresh mode shown in FIG. 10A again, the holes in the i-layer are removed. Hence, in the next conversion mode, a current proportional to light flows again.

In the above-described refresh mode shown in FIG. 10A, all holes in the i-layer are ideally removed. However, an effect is obtained even when the holes are partially removed. No problem arises because the same current as described above can be obtained. More specifically, it is only necessary to avoid the saturated state in FIG. 10C for detection in the next conversion mode. It is only necessary to determine the potential of the D electrode relative to the G electrode in the refresh mode, the period of the refresh mode, and the characteristic of the N+ layer serving as an injection inhibition layer. Additionally, in the refresh mode shown in FIG. 10A, electron injection to the i-layer is no necessary condition. The potential of the D electrode relative to the G electrode is not limited to the negative potential. This is because when many holes stay in the i-layer, the electric field in the i-layer is applied in the direction to guide the holes to the D electrode even when the potential of the D electrode relative to the G electrode is positive. The characteristic of the N+ layer serving as an injection inhibition layer need not always allow electron injection to the i-layer.

Figure 17:
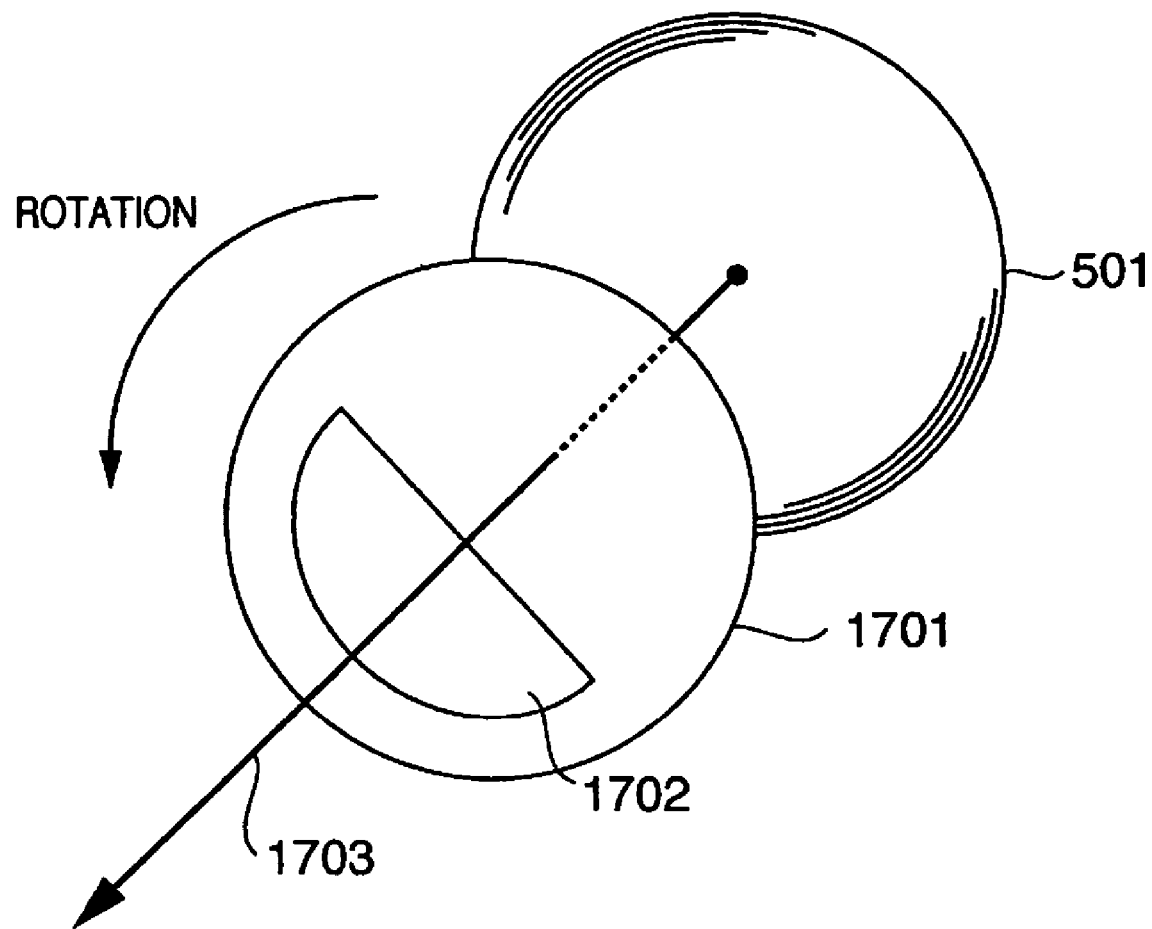
FIG. 17 is a schematic view showing another example in which the X-ray imaging apparatus is applied to an X-ray imaging system.

In this embodiment, the energy of X-rays is changed by switching the voltage (tube voltage) supplied from the X-ray power supply 504 to the X-ray tube 501. However, the present invention is not limited to this. As another method of changing the energy of X-rays, for example, a filter having regions with different X-ray absorbances is arranged between the X-ray tube 501 and the flat panel detector. FIG. 17 shows the example of the method. A filter 1701 absorbs the X-rays 1703 emitted from the X-ray tube 501. For example, the filter 1701 is rotated such that the passing timing of the X-rays 1703 passing through an opening 1702 of the filter 1701 synchronize with the irradiation timing of the irradiation pulse of the X-rays 1703. The energy of X-rays 170s arriving at the flat panel detector is switched in this manner.

In this embodiment, the energy of X-rays is switched between odd-numbered frame radiography and even-numbered frame radiography. However, the present invention is not limited to this. For example, the energy of X-rays for one of three frames may be switched. Alternatively, the energy of X-rays for one of four frames may be switched.

Second Embodiment

Figure 11:
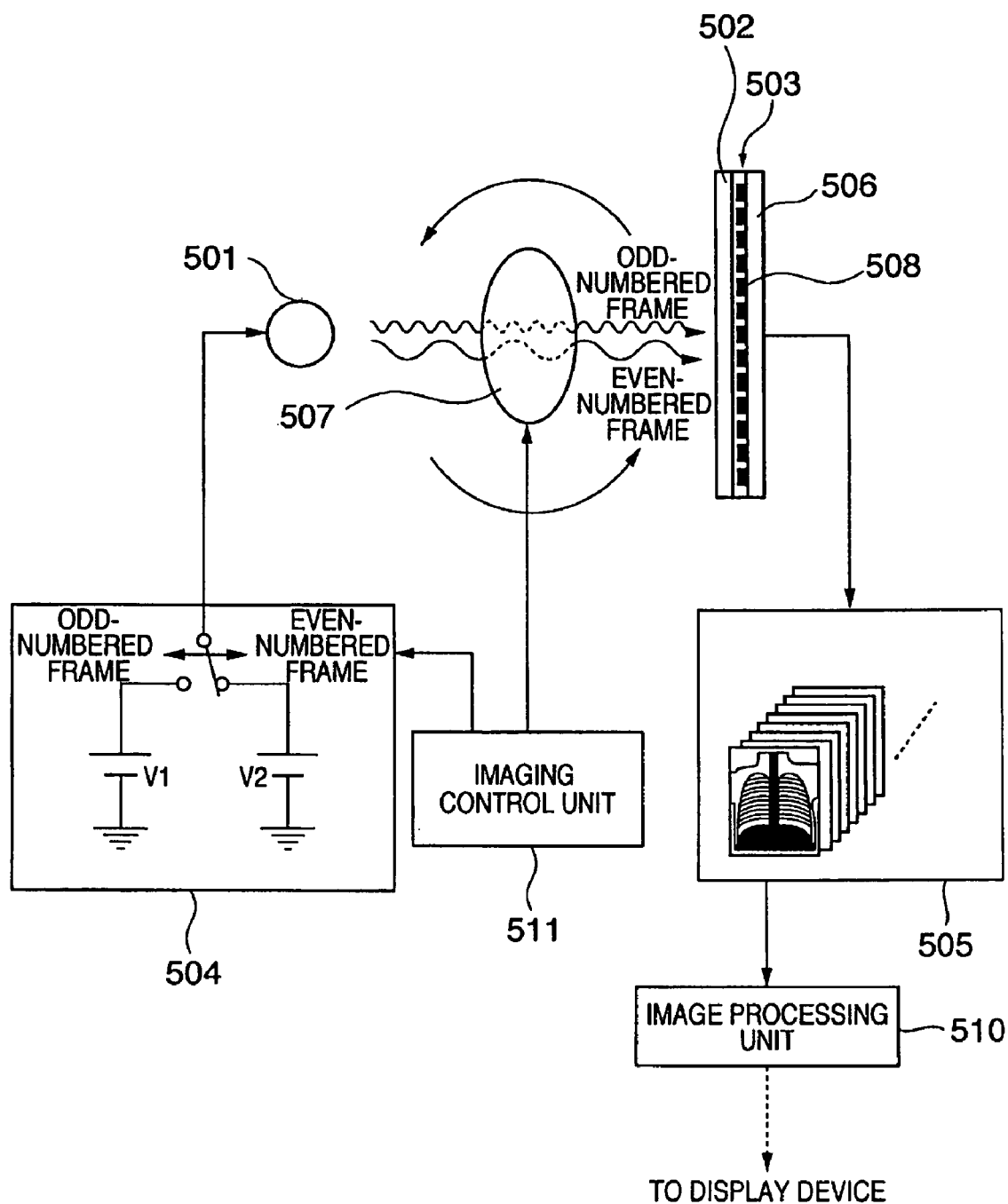
FIG. 11 is a view showing the schematic arrangement of an X-ray imaging apparatus according to the preferred second embodiment of the present invention.

FIG. 11 is a view showing the schematic arrangement of an X-ray imaging apparatus according to the preferred second embodiment of the present invention.

An object 507 is irradiated with X-rays which are emitted from an X-ray tube 501 and have an exit angle θ. The object 507 is mainly a human (patient). The X-rays transmitted through the object 507 are converted into visible light by a phosphor 502. The visible light from the phosphor 502 is converted into an electrical signal by conversion elements 508. As a result, an X-ray image of the object 507 is obtained as an electrical signal.

An example of the material of the conversion elements 508 is amorphous silicon. The conversion elements 508 are formed as pixels on an insulating substrate 506. The phosphor 502 and conversion elements 508 substantially adhere to each other by, e.g., bonding or the like so that an X-ray detection circuit 503 including the phosphor 502 and conversion elements 508 is formed. The phosphor 502 is made of a material containing at least one of, e.g., $Gd_2O_2S$, $Gd_2O_3$, CsI as the main component. An X-ray power supply 504 supplies a voltage to the X-ray tube 501. The X-ray power supply 504 supplies a high voltage to accelerate electrons in the X-ray tube 501.

In this embodiment, incident X-rays are converted into visible light by the phosphor 502. Without using the phosphor 502, incident X-rays may be absorbed by the conversion elements 508, and the absorbed X-rays may directly be converted into an electrical signal. In this case, the conversion elements 508 are made of a material containing at least one of, e.g., lead iodide, mercury iodide, selenium, cadmium telluride, gallium arsenide, gallium phosphide, zinc sulfide, and silicon as the main component.

A memory 505 stores, as digital data, the electrical signal (image signal) of the object 507 converted by the X-ray detection circuit 503 and has an area to store image data of a plurality of frames. The image data stored in the memory 505 is subjected to arithmetic processing such as energy subtraction processing and reconstruction processing to obtain a tomographic image by an image processing unit 510 so that an image for display or diagnosis is generated.

Even in the second embodiment, in executing temporally continuous radiography for a plurality of frames (n frames), an imaging control unit 511 switches the voltage to be supplied from the X-ray power supply 504 to the X-ray tube 501 between odd-numbered frame radiography and even-numbered frame radiography to change the wavelength of X-rays emitted from the X-ray tube 501, as in the first embodiment. The X-ray detection circuit 503 detects an image signal of the object 507 whose X-ray absorption of the internal structure changes. The detected image signal is converted into a digital signal by an A/D converter (not shown) and stored in the memory 505 as image data. In the example shown in FIG. 11, a voltage V1 is supplied from the X-ray power supply 504 to the X-ray tube 501 in odd-numbered frame radiography, while a voltage V2 is supplied in even-numbered frame radiography under the control of the imaging control unit 511. Hence, X-rays with a short wavelength are emitted from the X-ray tube 501 to the object 507 in odd-numbered frame radiography, while X-rays with a long wavelength are emitted in even-numbered frame radiography.

As a characteristic feature of the second embodiment, radiography is executed whole rotating the object 507 itself which is arranged between the X-ray tube 501 and the X-ray detection circuit 503. That is, the gantry 509 described in the first embodiment need not be provided. Radiography can be executed by using X-rays of plain radiography in a so-called general radiography room of a hospital provided that a rotating seat (to be described later) is prepared.

Even in the X-ray imaging apparatus of the second embodiment, the X-ray detection circuit 503 has a large area because the conversion elements 508 are two-dimensionally arranged. The rotation angle of the object 507 can be 180° or 360°. It is then supposed that the patient (object 507) rarely feels dizzy and sick. In this embodiment, the radiography time can be shortened as compared to the conventional helical scan CT. For example, in radiographing the chest part of a patient, the breath holding time required of him/her can be shortened. Hence, the burden on the patient can be reduced.

Figure 12:
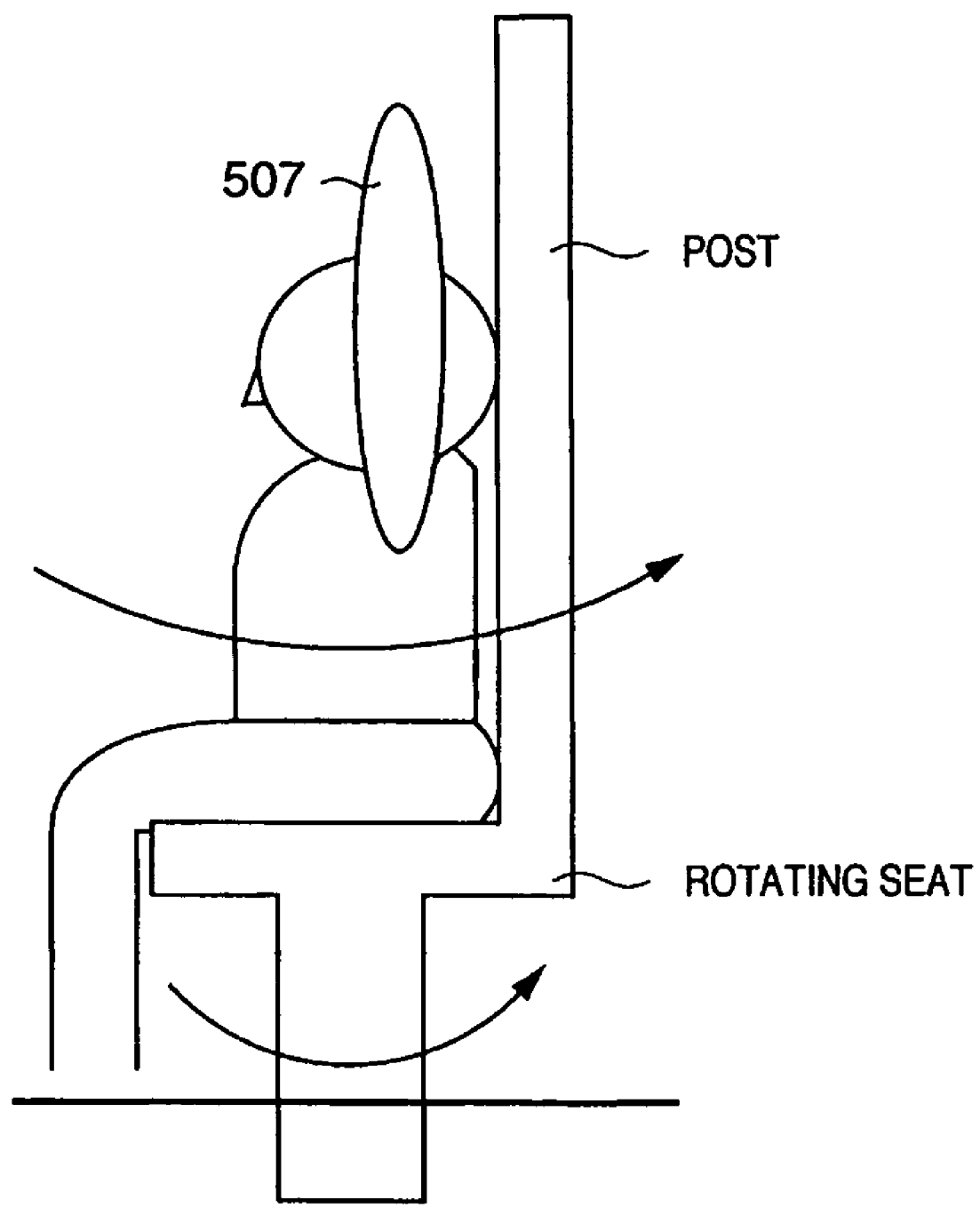
FIG. 12 is a schematic view showing a rotation mechanism to rotate an object in the X-ray imaging apparatus according to the preferred second embodiment of the present invention.

FIG. 12 is a schematic view showing a rotation mechanism to rotate the object 507 in the X-ray imaging apparatus according to the preferred second embodiment of the present invention. The rotation mechanism functions as a driving mechanism to change the positional relationship between the object 507 and the X-ray tube 501 and X-ray detection circuit 503. The object 507 who is placed on the rotating seat and fixed to the post is rotated by 180° or 360°. The object (patient) 507 in FIG. 12 holds the hands up for chest radiography. For, e.g. the head part, radiography is executed by setting the patient in another posture.

Third Embodiment

Figure 13:
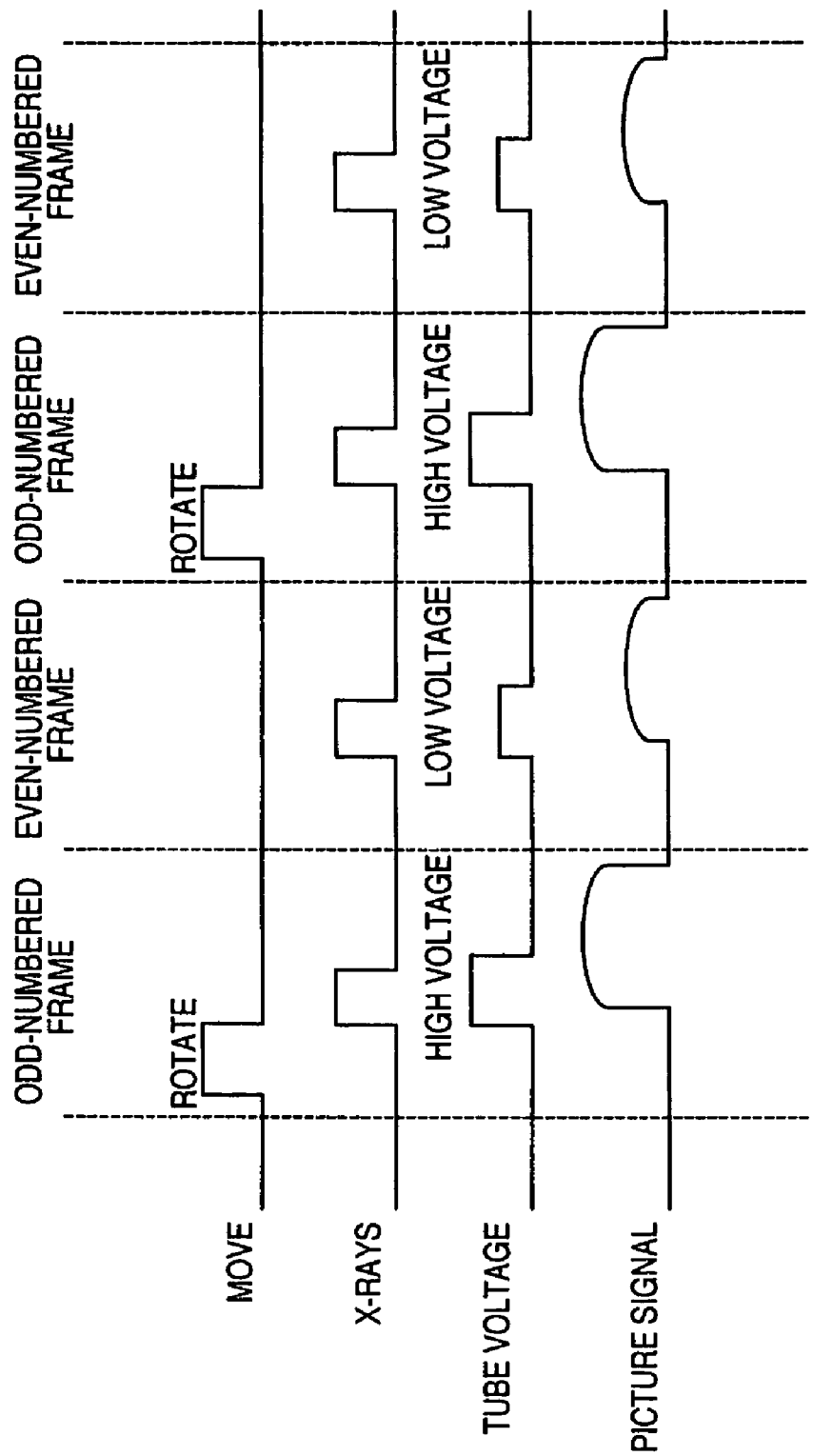
FIG. 13 is a timing chart showing the operation of an X-ray imaging apparatus according to the preferred third embodiment of the present invention.

FIG. 13 is a timing chart showing the operation of an X-ray imaging apparatus according to the preferred third embodiment of the present invention. The timing chart in FIG. 13 shows four signals: "move", "X-rays", "tube voltage" and "picture signal" in radiographing odd- and even-numbered frames. "Move" indicates the timing of rotation (displacement) of an object 507 which is arranged between an X-ray tube 501 and an X-ray detection circuit 503. As a characteristic feature of the third embodiment, the reading operation is executed in accordance with a sequence wherein movement is done in odd-numbered frame radiography but not in even-numbered frame radiography. Radiography is executed with one rotation for every two frames. More specifically, an imaging control unit 511 shown in FIG. 11 does not change the positional relationship between the object 507 and the X-ray tube 501 and X-ray detection circuit 503 in odd-numbered frame radiography for the (2m−1)th frame and even-numbered frame radiography for the (2m)th frame if the value m is the same. Every time the value m is incremented by one, the positional relationship between the object 507 and the X-ray tube 501 and X-ray detection circuit 503 is changed.

In this embodiment, odd-numbered frames and even-numbered frames are radiographed in the same positional relationship. For this reason, the accuracy of energy subtraction processing executed later by an image processing unit 510 increases. In the timing chart shown in FIG. 13, movement is done in odd-numbered frame radiography but not in even-numbered frame radiography. However, even when the timing of movement is reversed, the same effect can be obtained without any problem.

Fourth Embodiment

Figure 14:
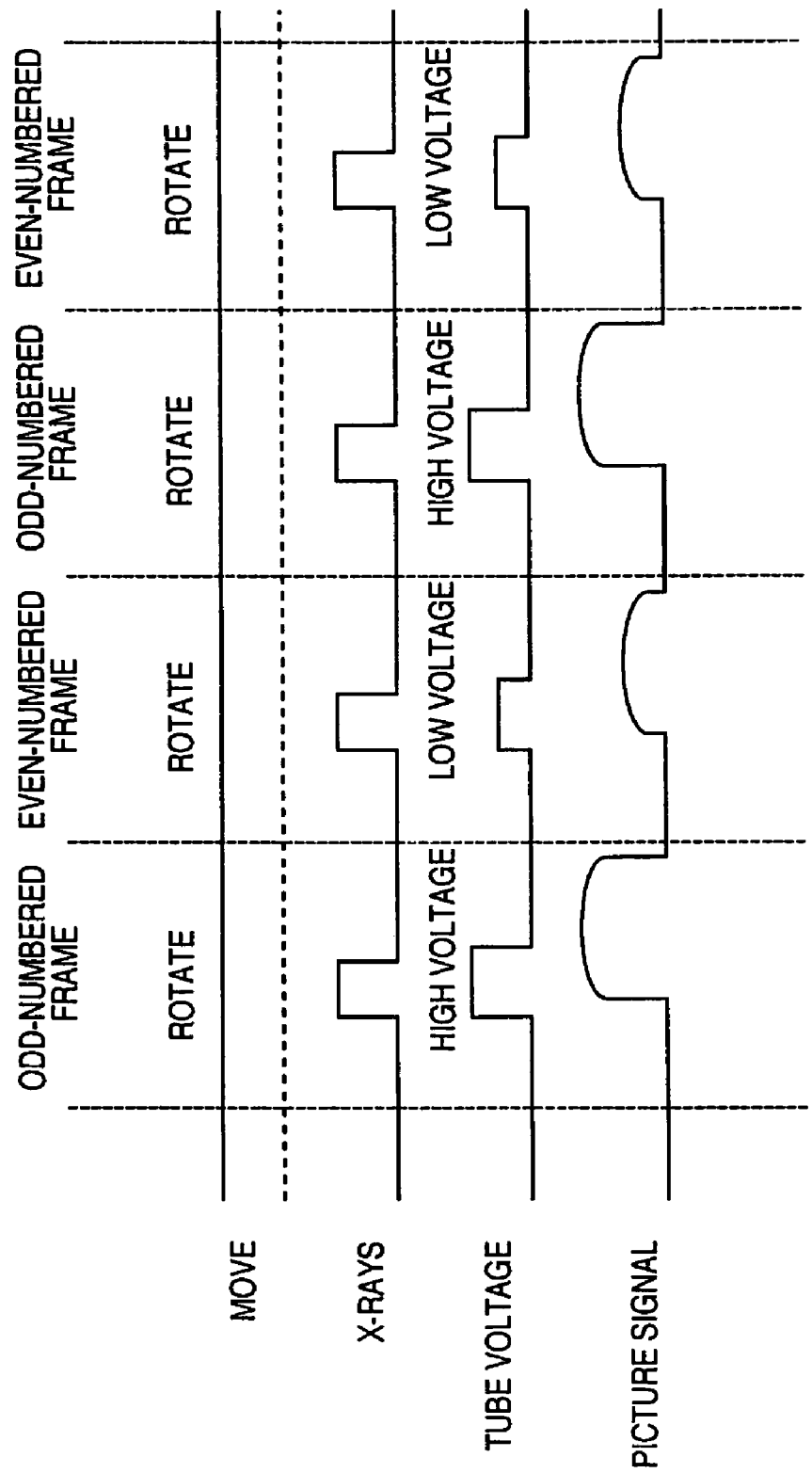
FIG. 14 is a timing chart showing the operation of an X-ray imaging apparatus according to the preferred fourth embodiment of the present invention.

FIG. 14 is a timing chart showing the operation of an X-ray imaging apparatus according to the preferred fourth embodiment of the present invention. The timing chart in FIG. 14 shows four signals: "move", "X-rays", "tube voltage" and "picture signal" in radiographing odd- and even-numbered frames. "Move" can be regarded as movement (displacement) of a pair of X-ray tube 501 and X-ray detection circuit 503, which rotates around an object 507 in FIGS. 1 and 2. Alternatively, "move" can be regarded as rotation (displacement) of the object 507 which is arranged between the X-ray tube 501 and the X-ray detection circuit 503 in FIG. 11. As a characteristic feature of FIG. 14, uniform rotational motion is performed independently of odd- or even-numbered frame radiography. In this embodiment, since no mechanism for pulse-like rotation is necessary, the load on the rotation mechanism such as a motor decreases.

Fifth Embodiment

Figure 15:
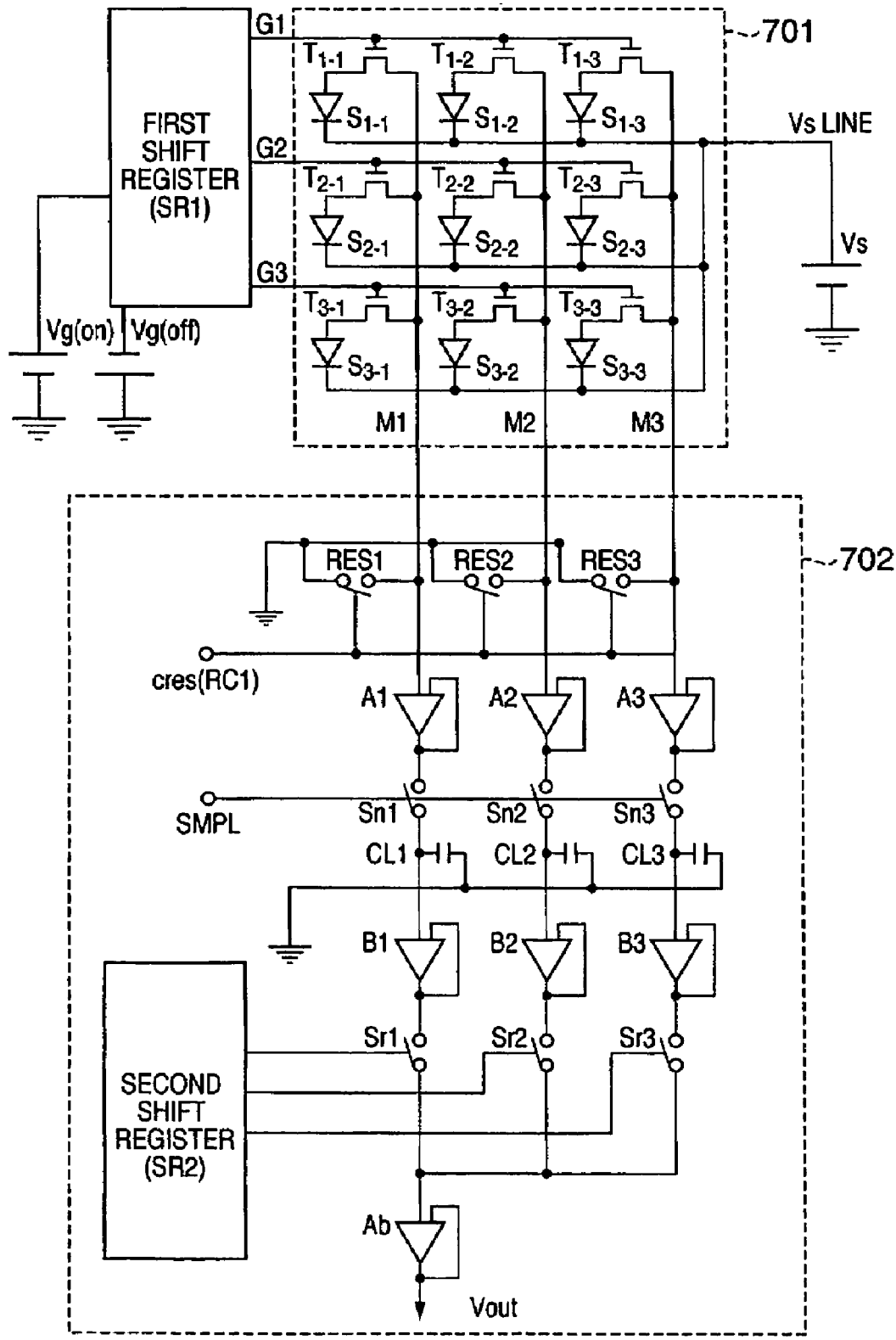
FIG. 15 is a circuit diagram of an X-ray detection circuit of an X-ray imaging apparatus according to the preferred fifth embodiment of the present invention.

FIG. 15 is a circuit diagram of an X-ray detection circuit of an X-ray imaging apparatus according to the preferred fifth embodiment of the present invention. FIG. 15 is different from FIG. 4 in that conversion elements S1-1 to S3-3 include not MIS sensors but p-i-n sensors. Since the p-i-n sensor can perform continuous radiography without the refresh operation, unlike the MIS sensor, the frame rate can generally be higher than that of the MIS sensor. Since the conversion elements S1-1 to S3-3 are formed from p-i-n sensors, a reading circuit 702 has an arrangement different from the reading circuit 707 in FIG. 4.

Sixth Embodiment

Figure 16:
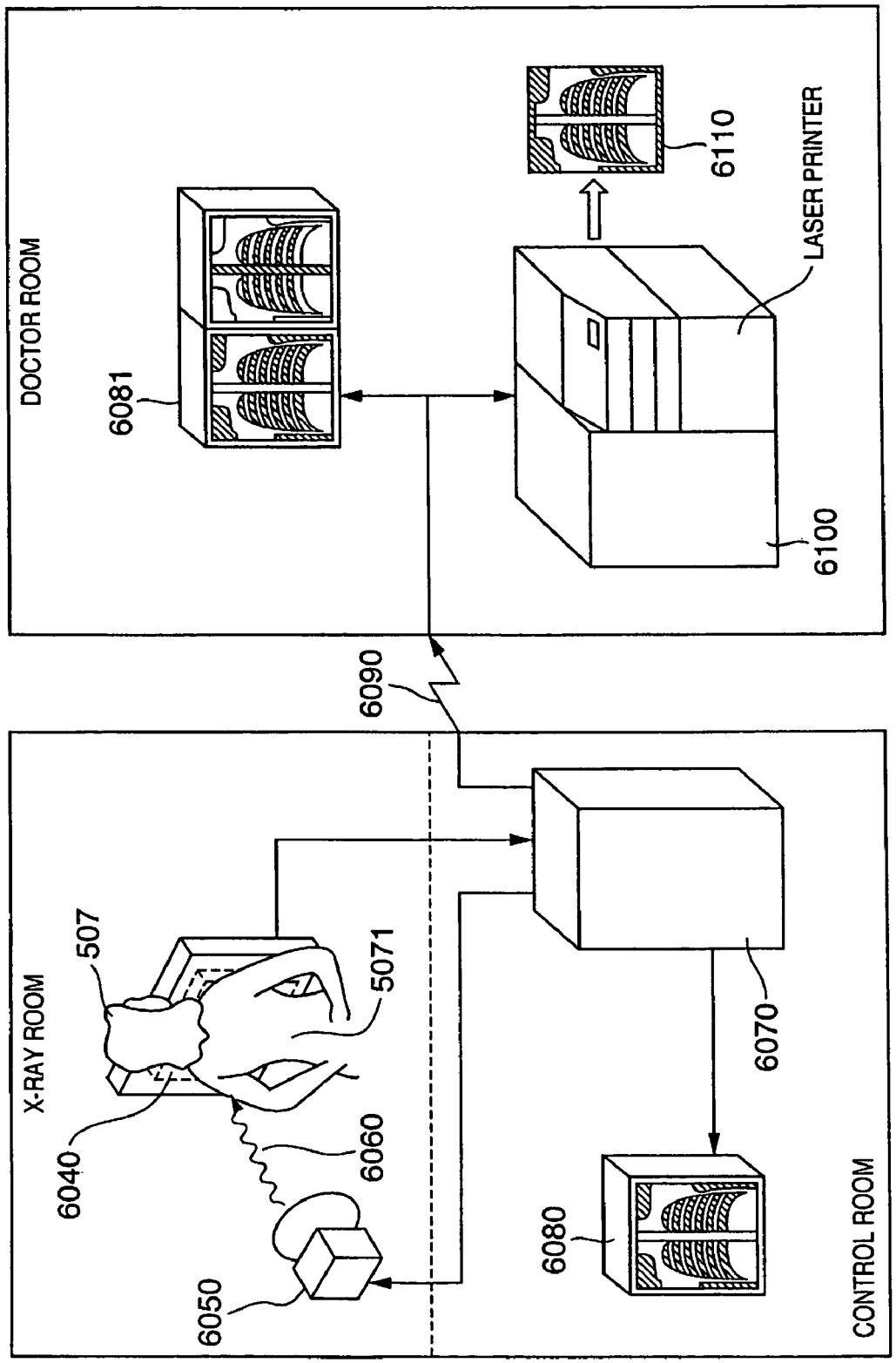
FIG. 16 is a schematic view showing the preferred sixth embodiment of the present invention in which an X-ray imaging apparatus is applied to an X-ray imaging system.

FIG. 16 is a schematic view showing the preferred sixth embodiment of the present invention in which an X-ray imaging apparatus is applied to an X-ray imaging system. X-rays 6060 generated by an X-ray tube 6050 are transmitted through a chest part 5071 of an object 507 and become incident on an image sensor 6040. The X-rays incident on the image sensor 6040 contain information in the body of the object 507. In the image sensor 6040, the X-rays are converted into visible light by a phosphor in correspondence with incident of the X-rays. The visible light is photoelectrically converted to obtain an electrical signal. The electrical signal is converted into digital data, subjected to image processing by an image processor 6070 serving as a signal processing unit, and displayed and observed, as an image, on a display 6080 serving as a display unit in the control room.

The X-ray tube 6050 of this embodiment corresponds to, e.g., the X-ray tube 501 in FIG. 1. The image sensor 6040 corresponds to, e.g., the X-ray detection circuit 503 in FIG. 1. The image processor 6070 corresponds to, e.g., the X-ray power supply 504, imaging control unit 511, memory 505, and image processing unit 510 in FIG. 1.

Image data generated by image processing of the image processor 6070 can be transferred to a remote site by a transmission unit 6090 such as a telephone line. The image data can also be displayed on a display 6081 serving as a display unit or stored in a storage unit such as an optical disk in another location such as a doctor room. Hence, diagnosis by a doctor in a remote site is also possible. The image data can also be recorded as a film 6110 by using a film processor 6100.

The object 507 and image sensor 6040 in FIG. 16 are illustrated as if they were adhered to each other. However, an X-ray imaging apparatus which executes tomography while rotating the object 507 as shown in FIGS. 11 and 12 can also be applied to the X-ray imaging system.

According to the preferred embodiments of the present invention, in capturing a plurality of continuous X-ray images of the object 507, the imaging control unit 511 controls the voltage of the X-ray power supply 504 to change the wavelength of the X-rays emitted from the X-ray tube 501 between odd-numbered frame radiography for the (2m−1)th (m is a natural number; m≧1) frame and even-numbered frame radiography for the (2m)th frame. In addition, driving of the driving mechanism (e.g., the gantry 509 shown in FIG. 1 or the rotation mechanism shown in FIG. 12) to change the positional relationship between the object 507 and the X-ray tube 501 and X-ray detection circuit unit 510 processes the image data of the odd-numbered frame and the image data of the even-numbered frame stored in the memory 505 to generate a tomographic image or 3D image of the object 507. As a result, an image without, e.g., the shadow of a bone with a high contrast can be obtained from a radiographic image of a complex structure including parts such as bones and blood vessels with different radiation absorptions. Hence, a morbid portion with a very low contrast near a structure with a high contrast can be detected, and the diagnostic efficiency can be increased.

The X-ray detection circuit 503 having a large area is formed by two-dimensionally arranging the conversion elements 508. When a rotation mechanism to rotate the object 507 as shown in FIGS. 11 and 12 is employed, an X-ray imaging system having an economical X-ray imaging apparatus with a high space factor can be implemented, as shown in FIG. 16. This X-ray imaging system facilitates recording, display, printing, and storage of obtained radiographic data. A brand-new X-ray imaging system that meets the requirements of recent digitization and replaces conventional systems of film radiographic scheme can be provided. Hence, an advanced medical environment with higher quality than now can be realized in aging societies of the future.

The X-ray tube 501 emits X-rays in a conical shape (so-called cone beam) with the exit angle (cone angle) θ to the object 507. In addition, since the X-ray detection circuit having a large area is formed by two-dimensionally arranging the conversion elements 508, the radiography time can be shortened, and the burden on an object (patient) can be reduced. For example, in radiographing the chest part of a patient, the breath holding time required of him/her can be shortened.

As many apparently widely different embodiments of the present invention can be made without departing from the spirit and scope thereof, it is to be understood that the invention is not limited to the specific embodiments thereof except as defined in the claims.

This application claims the benefit of Japanese Patent Application No. 2005-174095 filed on Jun. 14, 2005 and Japanese Patent Application No. 2006-157467 filed on Jun. 6, 2006, which are hereby incorporated by reference herein in its entirety.

What is claimed is:
1. A radiographic imaging apparatus comprising:
a radiation detection circuit in which a plurality of conversion elements to convert radiation emitted from a radiation source and transmitted through an object into an electrical signal are arranged two-dimensionally;

a driving mechanism which changes a positional relationship between the object and the radiation source and said radiation detection circuit;

a memory which stores, as image data, the electrical signal detected by said radiation detection circuit;

an imaging controller configured to control the radiation source so as to emit a first radiation pulse at a first energy when imaging a first frame and to emit a second radiation pulse at a second energy when imaging a second frame, and to control said driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period, wherein the second frame is different from the first frame and the first and second frames are sequentially imaged; and an image processing unit which executes subtraction processing of image data of the first frame and image data of the second frame stored in said memory to generate a processed image and generates one of a tomographic image and a 3D image of the object by using the processed image.

2. The apparatus according to claim 1, further comprising a display device which displays one of the tomographic image and the 3D image of the object generated by said image processing unit.

3. The apparatus according to claim 1, wherein said imaging controller is configured to control the radiation source so as to emit a third radiation pulse at the first energy when imaging a third frame, and to control said driving mechanism so as to maintain the positional relationship during a third period in which the third radiation pulse is emitted and to maintain the positional relationship in a period, during which neither the first radiation pulse nor second radiation pulses is emitted, between the second period and the third period, wherein the second frame is sequentially imaged after the first image is imaged, and the third frame is sequentially imaged after the second image is imaged.

4. The apparatus according to claim 1, wherein the radiation is emitted from the radiation source to the object in a conical shape.

5. The apparatus according to claim 1, wherein
the object is arranged between the radiation source and said radiation detection circuit, and
said driving mechanism changes the positional relationship by rotating the object.

6. The apparatus according to claim 5, wherein said driving mechanism rotates the object by 180° or 360°.

7. The apparatus according to claim 1, wherein
the object is arranged between the radiation source and said radiation detection circuit, and
said driving mechanism changes the positional relationship by integrally rotating the radiation source and said radiation detection circuit around the object.

8. The apparatus according to claim 7, wherein said driving mechanism integrally rotates the radiation source and said radiation detection circuit around the object by 180° or 360°.

9. The apparatus according to claim 1, wherein
said radiation detection circuit has a wavelength convener which converts the radiation emitted from the radiation source into visible light, and the conversion element converts the visible light converted by said wavelength converter into the electrical signal.

10. The apparatus according to claim 1, wherein the first frame and the second frame are an odd-numbered frame and an even-numbered frame, respectively, which are consecutive.

11. The apparatus according to claim 1, wherein said imaging control unit changes a waveform of the radiation emitted from the radiation source.

12. The apparatus according to claim 1, wherein a voltage to be supplied from a power supply is controlled.

13. A radiographic imaging system comprising:
a radiographic imaging apparatus of claim 1;
signal processing means for processing a signal from said radiographic imaging apparatus;
display means for displaying the signal from said signal processing means; and
transmission means for transmitting the signal from said signal processing means.

14. A radiographic imaging apparatus comprising:
a radiation detection circuit in which a plurality of conversion elements to convert radiation emitted from a radiation source and transmitted through an object into an electrical signal are arranged two-dimensionally;
a driving mechanism which changes a positional relationship between the object and the radiation source and said radiation detection circuit;
a memory which stores, as image data, the electrical signal detected by said radiation detection circuit;
an imaging controller configured to control the radiation source so as to emit a first radiation pulse at a first energy when imaging a first frame and to emit a second radiation pulse at a second energy when imaging a second frame, and to control said driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period,
wherein the second frame is different from the first frame and the first and second frame are sequentially imaged; and
an image processing unit configured to generate at least two of a first image based on image data of the first frame stored in said memory, a second image based on image data of the second frame stored in said memory, and a processed third image based on image data obtained by executing energy subtraction processing for the image data of the first frame and the image data of the second frame and display the generated image on a display device.

15. A radiographic imaging system comprising:
a radiographic imaging apparatus of claim 14;
signal processing means for processing a signal from said radiographic imaging apparatus;
display means for displaying the signal from said signal processing means; and
transmission means for transmitting the signal from said signal processing means.

16. A control method of a radiographic imaging apparatus including a radiation detection circuit in which a plurality of conversion elements to convert radiation emitted from a radiation source and transmitted through an object into an electrical signal are arranged two-dimensionally, a driving mechanism which changes a positional relationship between the object and the radiation source and the radiation detection circuit, and a memory which stores, as image data, the electrical signal detected by the radiation detection circuit, comprising steps of:

controlling the radiation source so as to emit a first radiation pulse at a first energy when imaging a first frame and to emit a second radiation pulse at a second energy when imaging a second frame, wherein the second frame is different from the first frame and the first and second frame are sequentially imaged; and controlling said driving mechanism so as to maintain the positional relationship during a first period in which the first radiation pulse is emitted and during a second period in which the second radiation pulse is emitted and to change the positional relationship in a period, during which neither the first radiation pulse nor second radiation pulses is emitted, between the first period and the second period; and executing subtraction processing of image data of the first frame and image data of the second frame stored in said memory to generate a processed image and generating one of a tomographic image and a 3D image of the object by using the processed image.

* * * * *

UNITED STATES PATENT AND TRADEMARK OFFICE
CERTIFICATE OF CORRECTION

| | |
|---|---|
| PATENT NO. | : 7,386,089 B2 |
| APPLICATION NO. | : 11/450577 |
| DATED | : June 10, 2008 |
| INVENTOR(S) | : Tadao Endo et al. |

It is certified that error appears in the above-identified patent and that said Letters Patent is hereby corrected as shown below:

SHEET 3:

Figure 3, "APICTURE" should read --PICTURE--.

COLUMN 2:

Line 63, "above described" should read --above-described--.

COLUMN 3:

Line 6, "two dimensionally," should read --two-dimensionally,--;
    Line 20, "pulses" should read --pulse--;
    Line 34, "two dimensionally," should read --two-dimensionally--; and
    Line 48, "pulses" should read --pulse--.

COLUMN 4:

Line 6, "two dimensionally," should read --two-dimensionally,--; and
    Line 22, "pulses" should read --pulse--.

COLUMN 8:

Line 51, "chest plain" should read --ordinary chest--.

COLUMN 12:

Line 2, "number of" should be deleted.

COLUMN 17:

Line 64, "doctor" should read --doctor's--.

COLUMN 18:

Line 17, "unit" should read --503 is controlled.--; and
    Line 18, "510" should read --Furthermore, the image processing unit 510--.

UNITED STATES PATENT AND TRADEMARK OFFICE
CERTIFICATE OF CORRECTION

PATENT NO. : 7,386,089 B2
APPLICATION NO. : 11/450577
DATED : June 10, 2008
INVENTOR(S) : Tadao Endo et al.

It is certified that error appears in the above-identified patent and that said Letters Patent is hereby corrected as shown below:

COLUMN 19:

Line 16, "pulses" should read --pulse--;
Line 38, "pulses" should read --pulse--; and
Line 65, "convener" should read --converter--.

COLUMN 20:

Line 41, "pulses" should read --pulse--; and
Line 44, "frame" should read --frames--.

COLUMN 21:

Line 11, "frame" should read --frames--.

COLUMN 22:

Line 5, "pulses" should read --pulse--.

Signed and Sealed this

Seventeenth Day of February, 2009

JOHN DOLL
*Acting Director of the United States Patent and Trademark Office*